(12) United States Patent
Maeda et al.

(10) Patent No.: US 7,566,698 B2
(45) Date of Patent: Jul. 28, 2009

(54) 2-O-(β-D-GLUCOPYRANOSYL) ASCORBIC ACID, PROCESS FOR ITS PRODUCTION, AND FOODS AND COSMETICS CONTAINING COMPOSITIONS COMPRISING IT

(75) Inventors: Mitsuru Maeda, Shiga (JP); Masahiro Nakao, Kyoto (JP); Harukazu Fukami, Kyoto (JP)

(73) Assignee: Suntory Holdings Limited, Osaka (JP)

( * ) Notice: Subject to any disclaimer, the term of this patent is extended or adjusted under 35 U.S.C. 154(b) by 0 days.

(21) Appl. No.: 10/500,334

(22) PCT Filed: Dec. 27, 2002

(86) PCT No.: PCT/JP02/13857

§ 371 (c)(1),
(2), (4) Date: Dec. 30, 2004

(87) PCT Pub. No.: WO03/057707

PCT Pub. Date: Jul. 17, 2003

(65) Prior Publication Data

US 2005/0113312 A1    May 26, 2005

(30) Foreign Application Priority Data

Dec. 28, 2001   (JP)   ............... 2001-400258

(51) Int. Cl.
*A01N 43/04*   (2006.01)
*A01N 43/08*   (2006.01)
*C07H 15/00*   (2006.01)
*C07H 15/06*   (2006.01)

(52) U.S. Cl. ............... 514/27; 514/474; 536/4.1; 536/18.2

(58) Field of Classification Search ............... 536/4.1, 536/18.2; 514/27
See application file for complete search history.

(56) References Cited

U.S. PATENT DOCUMENTS 4,754,026 A * 6/1988 Kawada et al. ............ 536/28.5
5,407,812 A * 4/1995 Sakai et al. ................. 435/75
6,238,672 B1 * 5/2001 Chen ........................ 424/728

FOREIGN PATENT DOCUMENTS

| | | | |
|---|---|---|---|
| EP | 0 667 162 A | | 8/1995 |
| EP | 0 875 246 A | | 11/1998 |
| EP | 0 875 514 A | | 11/1998 |
| EP | 0 919 218 A | | 6/1999 |
| EP | 0 919 218 A1 | * | 6/1999 |
| EP | 1 145 709 A | | 10/2001 |
| JP | 53-98954 | * | 8/1978 |
| JP | 53-98954 A | | 8/1978 |
| JP | 07-252160 A | | 10/1995 |
| JP | 07252160 A | * | 10/1995 |

OTHER PUBLICATIONS

Norio Muto et al., "Formation of a Stable Ascorbic Acid 2-Glucoside by Specific Transglucosylation with Rice Seed α-Glucosidase," Agric. Biol. Chem., 54 (7), pp. 1697-1703, 1990, Agricultural Chemical Society of Japan, Tokyo, Japan.

* cited by examiner

*Primary Examiner*—Traviss C McIntosh, III
(74) *Attorney, Agent, or Firm*—Drinker Biddle & Reath LLP

(57) ABSTRACT

The present invention provides a novel ascorbic acid derivative as a provitamin C with improved stability in the body and prolonged life in the body compared to conventionally known 2-O-(α-D-glucopyranosyl)ascorbic acid. The composition comprising the novel compound 2-O-(β-D-glucopyranosyl) ascorbic acid has been extracted from plants such as from Ningxia *Lycium barbarum* L. and/or *Lycium chinense* Mill. The compositions comprising 2-O-(β-D-glucopyranosyl) ascorbic acid may be enzymatically synthesized using β-D-glucosyltransferase. Pure 2-O-(β-D-glucopyranosyl)ascorbic acid may be produced from such compositions. Alternatively, 2-O-(β-D-glucopyranosyl)ascorbic acid may be produced by chemical synthesis. The 2-O-(β-D-glucopyranosyl)ascorbic acid results in higher stability and a prolonged life of vitamin C when ingested in the body compared to the corresponding α-D-glucopyranosyl derivative, and is therefore highly suitable as a provitamin C to be used in cosmetics and foods.

11 Claims, 11 Drawing Sheets

Fig. 4 (Continuation)
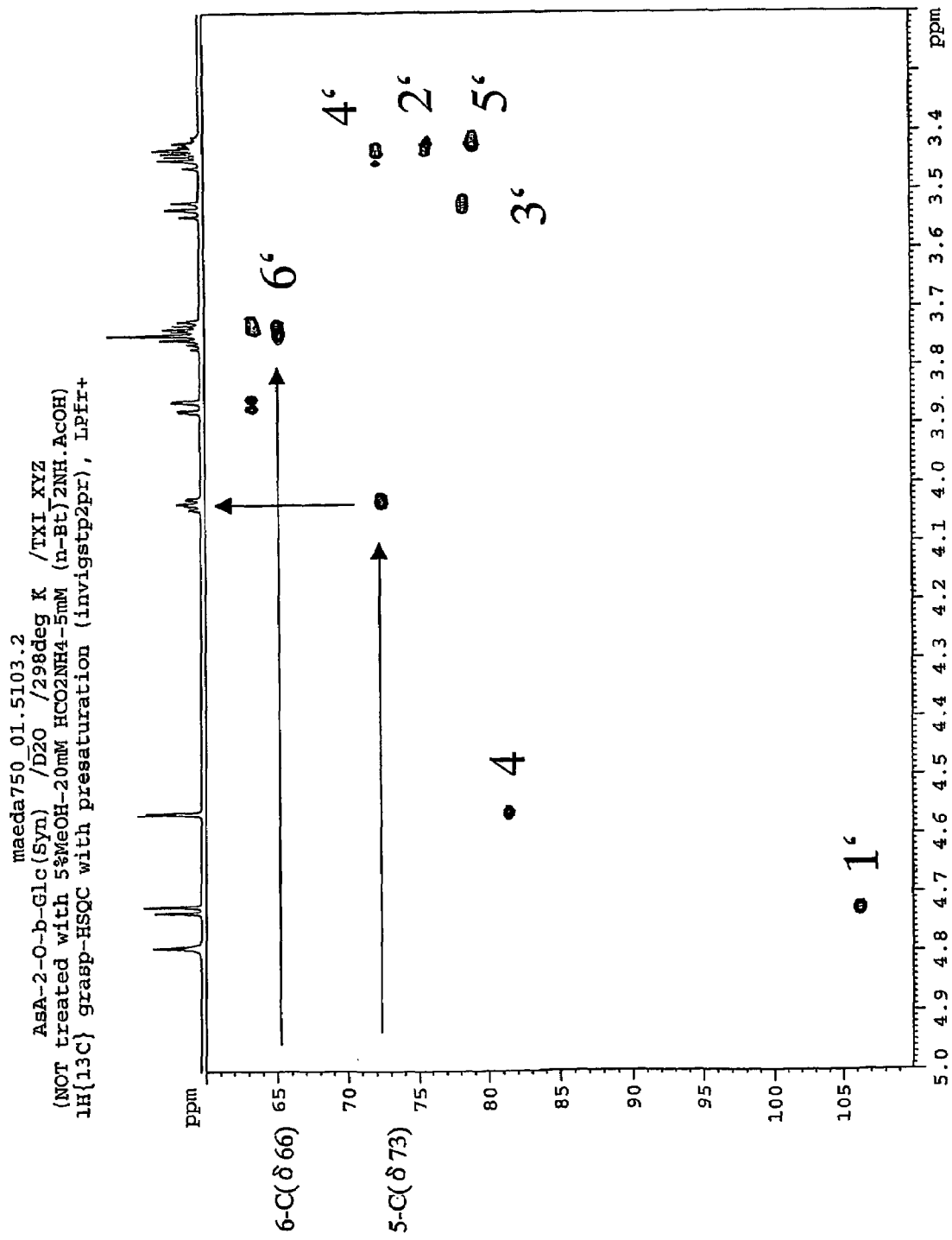

2-O-(β-D-GLUCOPYRANOSYL) ASCORBIC ACID, PROCESS FOR ITS PRODUCTION, AND FOODS AND COSMETICS CONTAINING COMPOSITIONS COMPRISING IT

FIELD OF THE INVENTION

The present invention relates to a novel provitamin C, 2-O-(β-D-glucopyranosyl)ascorbic acid, which has an increased stability, an extended half-life and a long lasting activity in the body compared to known provitamin C substances such as 2-O-(α-D-glucopyranosyl)ascorbic acid. The invention further relates to a novel intermediate, 2-O-(tetra-O-acetyl-β-D-glucopyranosyl)ascorbic acid, to a production process for 2-O-(β-D-glucopyranosyl)ascorbic acid using the 2-O-(tetra-O-acetyl-β-D-glucopyranosyl)ascorbic acid derivative as an intermediate, to a production process for 2-O-(β-D-glucopyranosyl)ascorbic acid extracted from a plant, and particularly a production process for 2-O-(β-D-glucopyranosyl)ascorbic acid extracted from a plant of Lycium genuse, L. chinense Mill., L. barbarum L. or its-related species, to compositions comprising the obtained 2-O-(β-D-glucopyranosyl)ascorbic acid, to an enzymatic production process for 2-O-(β-D-glucopyranosyl)ascorbic acid or compositions comprising 6-O-(β-D-glucopyranosyl) ascorbic acid and 2-O-(β-D-glucopyranosyl)ascorbic acid, and to the use of such compositions as foods or cosmetics.

PRIOR ART

Vitamin C is known to have numerous physiological effects, such as collagen synthesis, the lack of which is the major causative factor of scurvy, acting as a biological antioxidant to eliminate free radicals produced in the body and contributing to the iron ion oxidation-reduction reaction of cytochrome C, as well as having anticancer, immunoactivating, and cholesterol production-inhibiting and therefore antiarteriosclerotic effects. For skin, it exhibits various effects including photoaging inhibition, ultraviolet damage prevention and pigmentation inhibition, through antioxidation and collagen synthesis promotion, and is therefore used as an additive in cosmetic products (Fragrance Journal, Vol. 25, Special Issue, March 1997). It is also added to foods and cosmetics as an antioxidant. One of the major drawbacks of vitamin C is its extreme instability with respect to light, heat, oxygen and metal ions.

Various modifications have been studied to improve the instability of vitamin C or alter its properties to improve its retention and absorption in the body (Nihon Rinsho, Vol.57, No.10, p.170, 1999)

It has been attempted to introduce substituents at the hydroxyl groups of the 2,3-enediol, which is the antioxidizing moiety of vitamin C and the source of its instability, toward the aim of developing a more stable form of vitamin C known as "provitamin C". Examples include introduction of sulfate groups (Biochemistry, 8, 2652, 1969) or phosphate groups (Gazz. Chim. Ital., 91, 964, 1961 and Chem. Pharm. Bull., 17, 381, 1969) at the 2-hydroxyl position. Such compounds have greatly enhanced stability compared to ordinary vitamin C, and are known to be converted to vitamin C by in vivo and intracellular hydrolysis by sulfatases or phosphatases. These derivatives are already used in cosmetics and quasi drugs. Stable forms of vitamin C are also known which are glycosylated at the 2- or 3-hydroxyl groups. These include 2-O-(α-D-glucopyranosyl)ascorbic acid obtained with glycosyl-transferase (Biochim. Biophys. Acta, 1035, 44, 1990, Japanese Unexamined Patent Publication HEI Nos. 3-135992, 3-139288, 3-183492, 5-117290), 2-O-(β-D-galactopyranosyl)ascorbic acid obtained with galactosidase (Japanese Unexamined Patent Publication HEI No. 6-263790) and 3-O-(β-D-glucopyranosyl)ascorbic acid obtained by chemical synthesis (Japanese Unexamined Patent Publication SHO Nos. 53-98954, 58-198498), and the like.

Among these, most research has been conducted on 2-O-(α-D-glucopyranosyl)ascorbic acid, which is currently used in cosmetics and quasi drugs and under examination for approval as a food additive. 2-O-(α-D-Glucopyranosyl) ascorbic acid is, similar to ascorbyl-2-phosphate, highly stable under various oxidative conditions, and is much more stable under acidic conditions. When taken orally, 2-O-(α-D-glucopyranosyl)ascorbic acid is hydrolyzed by α-glucosidase present in the gastrointestinal mucosa and converted to the active form of vitamin C. It is also moderately hydrolyzed by enzymes present in the cell membranes of cultured cells whereby the action of vitamin C is exhibited continuously.

While unrelated to improvement in stability against oxidation, fatty acid esters of ascorbic acid at the 6-position, such as 6-O-palmitoyl and stearoylascorbic acids which are readily soluble in fat-soluble substances, are used as food antioxidants in food additives. Also, 6-glycosides have been synthesized enzymatically (Vitamins, 43, 205, 1971; Biochim. Biophys. Acta, 1035, 44, 1990; Japanese Unexamined Patent Publication HEI No. 5-320185). 5-Glycosides have also been disclosed, as by-products of 2-O-(α-D-glucopyranosyl) ascorbic acid by enzymatic synthesis (Japanese Unexamined Patent Publication HEI No. 5-112594).

Thus, numerous provitamin C substances are already known, but β-D-glucosides, particularly 2-O-glucoside substances, especially the novel 2-O-(β-D-glucopyranosyl) ascorbic acid compound of the present invention, have been unknown. And documents such as Japanese Unexamined Patent Publication HEI No. 3-13599, which discloses that β-D-glucopyranosyl L-ascorbic acid derivatives cannot be decomposed in the body, teach that β-glucosides cannot be utilized in the body and are therefore not useful.

Japanese Unexamined Patent Application No. Sho 53-98954 describes 2-O-(β-D-glucopyranosyl)ascorbic acid along with various ascorbic acid derivatives, but provides no concrete production examples, and it is believed that even with actual synthesis by the process in those examples, the 3-hydroxyl groups would be preferentially glucosylated, subsequently producing 2,3-diglucosides with glucosylation at the 2-position with respect to the 3-glucosylated product. It should therefore be impossible to obtain a product with β-glucosylation only at the 2-position.

The only report of enzymatic synthesis of β-D-glucopyranosyl L-ascorbic acid derivatives is that of production of 6-O-(β-D-glucopyranosyl)ascorbic acid by β-glucosidase from almond using cellobiose as the β-glucosyl donor (Agric. Biol. Chem., 54, 1697, 1990). In this case, the transfer yield of 6-O-(β-D-glucopyranosyl)ascorbic acid is a very low value of 1.5%, and there is no mention of production of 2-O-(β-D-glucopyranosyl)ascorbic acid. Thus, absolutely no case has been known where 2-O-(β-D-glucopyranosyl)ascorbic acid is synthesized by an enzymatic method.

Lycium chinense Mill. (Chinese matrimony-vine), a plant of the Solanaceae family, is listed as a delicacy in the ancient Chinese medical text "Compendium of Materia Medica", and the fruit thereof, known as lycii fructus and the leaves known as lycii folium are used as foods while the root skin, known as lycii cortex radicis, is used as a Chinese herbal medicine (Genshoku Wakanyaku Zukan [Illustrated Compendium of Oriental Drugs], Vol.I, 289, 1980). Lycium chinense Mill. contains betaine, carotene, nicotinic acid and zeaxanthin, and is known to have hypoglycemic, anti-hypertensive, lipotropic and hepatic function-protecting effects. In particular, the lipotropic and hepatic function-protecting effects are attributed to betaine, which acts as a methyl group donor (Folia Pharmacol. Japon, 56, 151, 1960). Also, a plant of *Lycium* genuse extract is known to promote the growth and acid production of lactic acid bacteria (C.A. 64:20530b, 1965). However, the presence of vitamin C derivatives among the components in a plant of *Lycium* genuse has been unknown.

SUMMARY OF THE INVENTION

As a result of extensive research focused on the myriad effects of a plant of *Lycium* genuse and its active components, the present inventors discovered a new substance contained therein, and completed one aspect of the invention by determining that the substance is 2-O-(β-D-glucopyranosyl)ascorbic acid. The invention therefore provides the novel substance 2-O-(β-D-glucopyranosyl)ascorbic acid, a composition comprising 2-O-(β-D-glucopyranosyl)ascorbic acid extracted from a plant of *Lycium* genuse and a process for their production.

The novel substance of the invention is useful as a provitamin C. β-Glucosidase is known to be present in membrane-bound form in small intestine tissue and in cytoplasmic form in hepatic and renal tissue (FEBS Letters, 436, 71, 1998), whereas α-glucosidase is widely distributed in saliva, intestinal digestive juices and the small intestinal tract where it presumably decomposes substrates to ascorbic acid upon peroral uptake. A report by Yamamoto et al. (J. Pharmacobio-Dyn. 13, 688, 1990) describes that only ascorbic acid is detected in the blood in an experiment with oral administration to rats, thus suggesting that instead of activation by α-glucosidase which is widely distributed in the body, decomposition and activation by β-glucosidase, which is less widely distributed, would be more advantageous in terms of the transport into tissues and long-lasting action; β-glucosides of provitamin C are therefore expected to exhibit even more desirable properties.

Upon studying the activity of the novel compound of the invention, 2-O-(β-D-glucopyranosyl)ascorbic acid, it was found to be highly useful as a provitamin C due to the improved stability and the prolonged effect in the body compared to 2-O-(α-D-glucopyranosyl)ascorbic acid. In addition, processes for its industrial production for utilization in foods and cosmetics were studied, and the invention was completed upon establishing a production process by chemical synthesis and extraction from natural plants, as well as an enzymatic production process.

Accordingly, the invention provides the novel substance 2-O-(β-D-glucopyranosyl)ascorbic acid, which has physiological action superior to that of 2-O-(α-D-glucopyranosyl)ascorbic acid and is expected to have applications in the fields of cosmetics, quasi drugs, medicines and foods, as well as 2-O-(tetra-O-acetyl-β-D-glucopyranosyl)ascorbic acid as a novel intermediate thereof, a process for production of 2-O-(β-D-glucopyranosyl)ascorbic acid by chemical synthesis through the intermediate, a process for production of compositions comprising 2-O-(β-D-glucopyranosyl)ascorbic acid by extraction from plants and especially from a plant of *Lycium* genuse, *L. chinense* Mill., *L. barbarum* L., a process for production of compositions comprising 2-O-(β-D-glucopyranosyl)ascorbic acid using β-D-glucosyltransferase, compositions comprising the obtained 2-O-(β-D-glucopyranosyl)ascorbic acid, and foods or cosmetics containing the compositions.

The invention further provides compositions comprising 2-O-(β-D-glucopyranosyl)ascorbic acid or 6-O-(β-D-glucopyranosyl)ascorbic acid obtained by the reaction using glycosyltransferase. It still further provides a method for easy removal of contaminants from solutions containing 2-O-(β-D-glucopyranosyl)ascorbic acid and an industrial scale production process of products with higher contents and higher purity of 2-O-(β-D-glucopyranosyl)ascorbic acid.

Throughout the present specification, the term "composition" will refer to any of various compositions comprising 2-O-(β-D-glucopyranosyl)ascorbic acid, including extracts with increased 2-O-(β-D-glucopyranosyl)ascorbic acid contents from plants containing 2-O-(β-D-glucopyranosyl)ascorbic acid, or reaction products containing 2-O-(β-D-glucopyranosyl)ascorbic acid which are obtained by reacting ascorbic acid and β-D-glucoside compounds using β-glucosyltransferase.

Throughout the present specification, the term "provitamin C" will collectively refer to compounds which themselves exhibit weak or no vitamin C activity but are decomposed in the body to produce vitamin C, as well as compositions comprising such compounds.

DESCRIPTION

Figure 1:
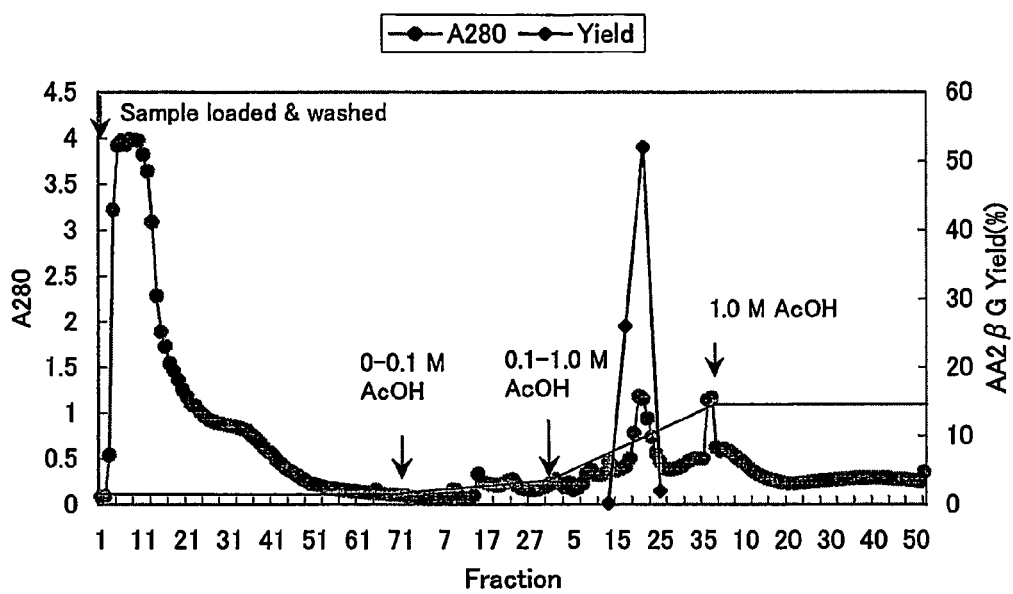
FIG. 1 is a graph showing the results of ion-exchange chromatography of 2-O-(β-D-glucopyranosyl)ascorbic acid extracted from *lycii fructus*.
Figure 2:
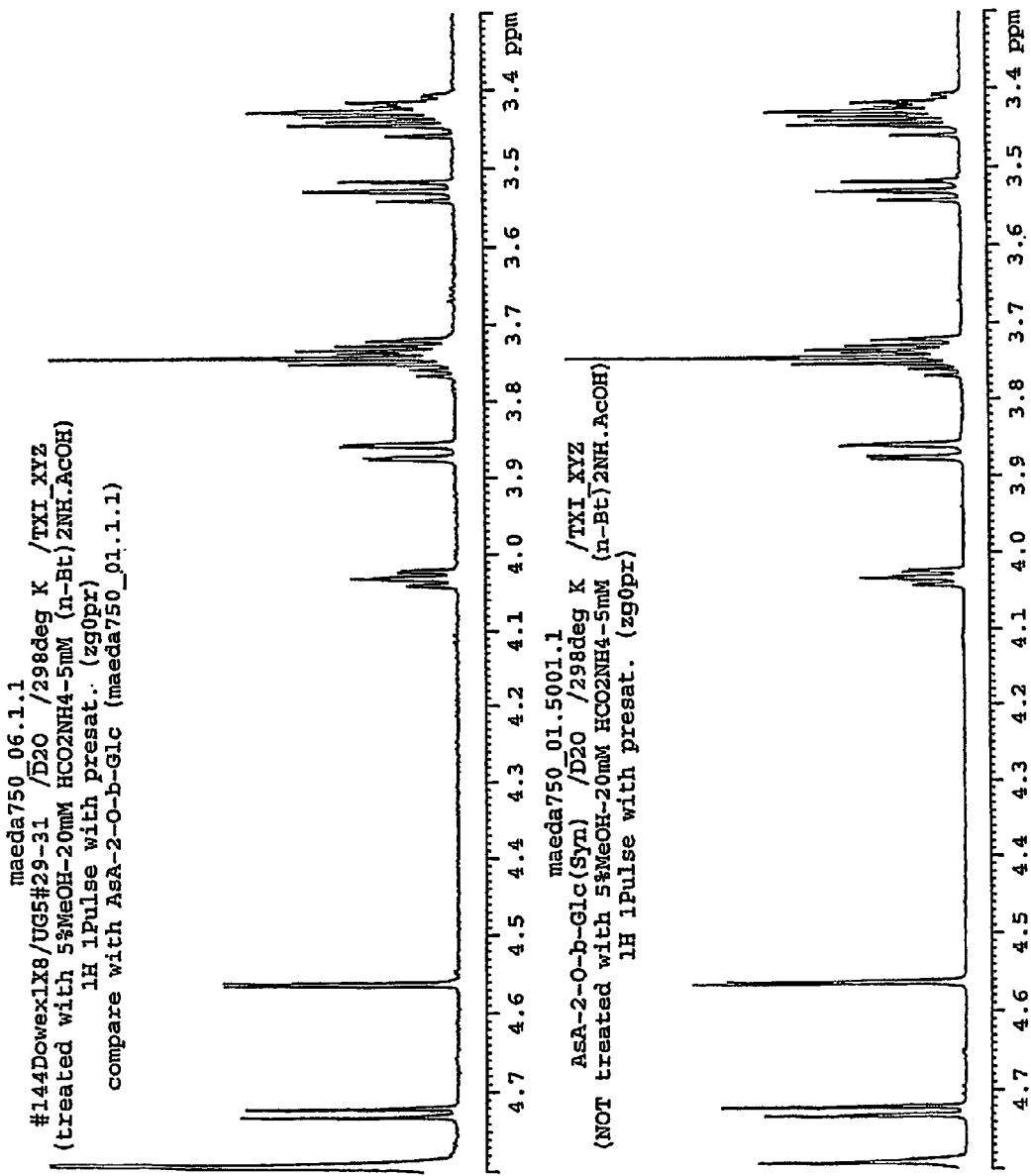
FIG. 2 shows the results of further purifying 2-O-(β-D-glucopyranosyl)ascorbic acid by high performance liquid chromatography using a portion of fractions 19-25 of FIG. 1, and comparing the $^1$H-NMR with a chemically synthesized product. The upper chart is the spectrum for *lycii fructus*-derived 2-O-(β-D-glucopyranosyl)ascorbic acid, and the lower chart is the spectrum for chemically synthesized 2-O-(β-D-glucopyranosyl)ascorbic acid.

The present inventors conducted extensive research on methods of synthesizing 2-O-(β-D-glucopyranosyl)ascorbic acid with the aim of creating the ideal provitamin C with the novel substance 2-O-(β-D-glucopyranosyl)ascorbic acid discovered in a plant of *Lycium* genuse, and found that chemical production is possible using 2-O-(tetra-O-acetyl-β-D-glucopyranosyl)ascorbic acid as an intermediate. Upon further ardent examination to search for plants and microbes containing 2-O-(β-D-glucopyranosyl)ascorbic acid, it was found that 2-O-(β-D-glucopyranosyl)ascorbic acid is present in a plant of *Lycium* genuse and *lycili fructus*. They also found that 2-O-(β-D-glucopyranosyl)ascorbic acid is produced by glycosyltransfer reaction of cellulase enzymes, and that 2-O-(β-D-glucopyranosyl)ascorbic acid is in fact an excellent provitamin C which exhibits notable inhibition of cell death upon ultraviolet B irradiation of human skin epidermal keratinocytes and notable promotion of collagen synthesis in normal human dermal fibroblasts, as compared to 2-O-(α-D-glucopyranosyl)ascorbic acid. The present invention has been completed upon these findings, and is based on the following.

Production of 2-O-(β-D-glucopyranosyl)ascorbic acid, which exhibits more excellent performance as a provitamin C than 2-O-(α-D-glucopyranosyl)ascorbic acid, can be achieved by a synthesis method using 2-O-(tetra-O-acyl-β-D-glucopyranosyl)ascorbic acid as an intermediate, by an extraction method from natural materials containing 2-O-(β-D-glucopyranosyl)ascorbic acid, and by an enzymatic synthesis method.

In the synthesis method, the 3-hydroxyl group of the corresponding ascorbic acid derivative is selectively benzylated to obtain 3-O-benzyl-5,6-O-isopropylideneascorbic acid, which is condensed with an ester-protected glucose 1-carbonate ester and then de-isopropylidenated and de-benzylated to obtain the product. In the extraction method from a natural material, a composition comprising 2-O-(β-D-glucopyranosyl)ascorbic acid may be obtained by extraction in hot water or water-alcohol from a plant of the family Solanaceae, and particularly the fresh fruit or dried fruit (*lycii fructus*) of a plant of *Lycium* genuse. If necessary, the 2-O-(β-D-glucopyranosyl)ascorbic acid may be further purified from such a composition. 2-O-(β-D-glucopyranosyl)ascorbic acid is also enzymatically synthesized by glycosyltransfer reaction of a cellulase to obtain a composition comprising 2-O-(β-D-glucopyranosyl)ascorbic acid. If necessary, the 2-O-(β-D-glucopyranosyl)ascorbic acid may be further purified from such a composition.

As it has been demonstrated by the present invention that 2-O-(β-D-glucopyranosyl)ascorbic acid notably inhibits cell death upon ultraviolet B irradiation of human skin epidermal keratinocytes and notably promotes collagen synthesis in normal human dermal fibroblasts, and that it is intracellularly converted to vitamin C and absorbed by oral ingestion, it is therefore expected to be useful as a skin cosmetic or skin protective agent and useful in foods as a provitamin C.

Preferred Embodiment

The invention provides 2-O-(β-D-glucopyranosyl)ascorbic acid, which has physiological action superior to 2-O-(α-D-glucopyranosyl)ascorbic acid and is expected to have applications in the fields of cosmetics, quasi drugs, medicines and foods, as well as 2-O-(tetra-O-acetyl-β-D-glucopyranosyl)ascorbic acid as an intermediate thereof, a process for production of 2-O-(β-D-glucopyranosyl)ascorbic acid using the intermediate, and 2-O-(β-D-glucopyranosyl)ascorbic acid-containing compositions comprising extracts from a plant of *Lycium* genuse, *L. chinense* Mill., *L. barbarum* L. or its-related species which contain 2-O-(β-D-glucopyranosyl) ascorbic acid.

The invention further provides compositions comprising 2-O-(β-D-glucopyranosyl)ascorbic acid or 6-O-(β-D-glucopyranosyl)ascorbic acid obtained by glucosyltransferase reaction. It still further provides a method for easy removal of contaminants from solutions containing 2-O-(β-D-glucopyranosyl)ascorbic acid and an industrial scale production process of products with higher contents and higher purity of 2-O-(β-D-glucopyranosyl)ascorbic acid.

The invention will now be explained in greater detail.

1) Synthesis of Intermediate: 2-O-(2,3,4,6-tetra-O-acyl-β-D-glucopyranosyl)ascorbic acid The intermediate 2-O-(2,3,4,6-tetra-O-acyl-β-D-glucopyranosyl)ascorbic acid may be synthesized in the following manner. Specifically, commercially available 5,6-O-isopropylideneascorbic acid is selectively benzylated at the 3-hydroxyl position by a known method (J. Med. Chem., 31, 793, 1988), to produce 3-O-benzyl-5,6-O-isopropylideneascorbic acid. This 3-O-benzylated compound as the aglycone is glycosylated by ordinary glycosylation reaction, to obtain 2-O-(2,3,4,6-tetra-O-acyl-β-D-glucopyranosyl)-3-O-benzyl-5,6-O-isopropylideneascorbic acid. For example, a (2,3,4,6-tetra-O-acetyl-β-D-glucopyranosyl)carbonic acid ester (Komura, H., Tokyo Institute of Technology doctoral thesis, 1977) may be obtained by heating at 100-200° C. together with the 3-O-benzylated compound in a nonpolar solvent or without a solvent. The carbonic acid ester used may be an alkyl-, halogenated alkyl- or optionally substituted aryl-carbonic acid ester. Alternatively, a (2,3,4,6-tetra-O-acetyl-β-D-glucopyranosyl)halide may be used for reaction in a halogenated hydrocarbon solvent such as chloroform or methylene chloride or an aromatic hydrocarbon solvent such as benzene or toluene, in the presence of a mercury salt or silver salt with addition of a dehydrating agent (Lodd's Chemistry of Carbon Compounds IF, 320, 1967, Elsevier).

The isopropylidene group of 2-O-(2,3,4,6-tetra-O-acyl-β-D-glucopyranosyl)-3-O-benzyl-5,6-O-isopropylideneascorbic acid may be hydrolyzed with an acid catalyst for its removal. For example, deisopropylidenation may be performed at 40-100° C. in a 30-80% acetic acid aqueous solution. Alternatively, it may be performed from room temperature to reflux temperature in acetone or methyl ethyl ketone in the presence of p-toluenesulfonic acid. Water may instead be used for the same reaction.

The benzyl group of the 2-O-(2,3,4,6-tetra-O-acyl-β-D-glucopyranosyl)-3-O-benzylascorbic acid may be removed by ordinary hydrogenolysis. For example, debenzylation may be accomplished in a protic polar solvent such as acetic acid or alcohol, or a non-polar solvent such as benzene, toluene or ethyl acetate, in the presence of hydrogen, using palladium-carbon, palladium black, platinum-carbon or platinum black as the catalyst.

The deprotection steps may be carried out in the reverse order. That is, after debenzylation reaction of the 2-O-(2,3,4,6-tetra-O-acyl-β-D-glucopyranosyl)-3-O -benzyl-5,6-O-isopropylideneascorbic acid, the resulting 2-O-(2,3,4,6-tetra-O-acetyl-β-D-glucopyranosyl)-5,6-O-isopropylideneascorbic acid may be deisopropylidenated with an acid catalyst.

The title intermediate, 2-O-(2,3,4,6-tetra-O-acyl-β-D-glucopyranosyl)ascorbic acid, may be obtained in the manner described above.

Acetyl is preferred as the acyl group of the title intermediate.

2) Chemical synthesis of 2-O-(β-D-glucopyranosyl)ascorbic acid

2-O-(β-D-Glucopyranosyl)ascorbic acid may be obtained by alkali hydrolysis of the acyl group of 2-O-(2,3,4,6-tetra-O-acyl-β-D-glucopyranosyl)ascorbic acid. The alkali used may be an aqueous solution of sodium hydroxide or potassium hydroxide, an aqueous solution of carbonate such as potassium carbonate, sodium carbonate, potassium bicarbonate or sodium bicarbonate, or a metal alcoholate such as sodium methylate. The solution may contain an alcohol such as methanol and ethanol to dissolve the 2-O-(2,3,4,6-tetra-O-acyl-β-D-glucopyranosyl)ascorbic acid as the starting material. The reaction temperature is optimally from 0° C. to room temperature. The reaction solution is neutralized with hydrochloric acid, sulfuric acid or a cation-exchange resin. In the case of hydrochloric acid or sulfuric acid it is necessary to remove the salt which is produced, but in the case of a cation-exchange resin no desalting procedure is required due to the adsorption of sodium and potassium salts. The neutralized solution may be lyophilized or concentrated under reduced pressure to obtain the desired compound. Depending on the purpose, the compound may be purified further by column chromatography.

3) Production of Composition Comprising 2-O-(β-D-glucopyranosyl)ascorbic acid by Extraction from a Plant of *Lycium* genuse. *L. chinense* Mill., *L. barbarum* L.

The fresh or dried fruit (*lycii fructus*) of a plant of *Lycium* genuse, *L. chinense* Mill., *L. barbarum* L. is immersed in an aqueous solvent such as hot water or aqueous ethanol either directly or after pulverization, and the extract obtained by solid/liquid separation is concentrated under reduced pressure or lyophilized, or else spray dried, to obtain an extract containing 2-O-(β-D-glucopyranosyl)ascorbic acid. The alcohol concentration during the immersion is preferably from 10-95%, and the immersion is preferably continued from 3 to 7 days.

The 2-O-(β-D-glucopyranosyl)ascorbic acid content in the *lycii fructus* extract will typically be from 0.86 to 1.2%, but a composition with an even higher content can be obtained by the method described hereunder. Specifically, the *lycii fructus* extract is dissolved in distilled water, or the extract obtained by immersing the starting material in 5-50 volumes and preferably 8-10 volumes of the solvent is diluted with distilled water, and then passed through a strongly basic anion exchange resin such as Dowex™ 1-X8 (Dow Chemical Co.) or Amberlite IRA-400 (Rohm & Haas Co.) for adsorption of the 2-O-(β-D-glucopyranosyl)ascorbic acid. After thorough washing with water, a fraction containing the desired substance is obtained by stepwise elution or gradient elution using an acid solution of acetic acid or the like. The fraction is concentrated under reduced pressure or lyophilized to remove acetic acid, thereby to yield a composition containing 2-O-(β-D-glucopyranosyl)ascorbic acid at approximately 30-50%.

4) Production of Composition Comprising 2-O-(β-D-glucopyranosyl)ascorbic acid by Enzyme Method As a result of extensive study on commercially available enzyme preparations, it was found that β-glucosyltransferase activity is exhibited by the enzyme preparations cellulase "Onozuka" and Pancelase BR (Yakult Pharmaceutical Ind. Co., Ltd.), Cellulosin (Hankyu Kyoei Bussan), Cellulase (Sigma), β-glucosidase (Toyobo) and β-glucosidase (Nacalai Tesque). The glycosyltransferase used for the invention may be any one which acts on solutions comprising β-glucosyl group-containing compounds and ascorbic acid to synthesize 2-O-(β-D-glucopyranosyl)ascorbic acid by glycosylation reaction, and the source and type is not limited; however, from the standpoint of yield, cellulases from *Trichoderma* and β-glucosidases from almond are preferred.

The cellobiose and ascorbic acid concentrations for the transferase reaction are preferably as high as possible, and preferably about 0.3 M and 0.2 M, respectively. The cellobiose as the enzyme substrate may be supplied as another β-glucosyl group-containing compound, such as a high molecular glucan such as cellulose or carboxymethyl cellulose in combination with an appropriate hydrolase. Each enzyme may be immobilized on a suitable support by an ordinary method to form an enzyme reactor to facilitate efficient production of 2-O-(β-D-glucopyranosyl)ascorbic acid. On the other hand, the ascorbic acid serving as the acceptor in the transfer reaction is preferably the free acid from the standpoint of stability and transfer yield in the reaction, but ascorbic acid may be used also in the form of a salt such as an alkali metal salt or an alkaline earth metal salt, or a mixture thereof. It was further discovered that isoascorbic acid, either the free acid form or a salt thereof, likewise act as the acceptor in the transfer reaction. Consequently, ascorbic acid or ascorbic acid derivatives may be used for the transglycosylation reaction depending on the purpose, and in most cases sodium ascorbate, calcium ascorbate and the like may be suitably used according to the need, instead of free ascorbic acid alone.

The enzyme reaction proceeds in aqueous solution in a pH range of 2-8, but preferably at pH 4-6 considering the optimum pH for the enzyme. The reaction temperature will be 20-60° C., but is preferably kept at about 30-40° C. considering the enzyme stability and optimum temperature. The amount of enzyme added is preferably 20-400 units (where 1 unit is the activity of the enzyme which liberates 1 μmol of p-nitrophenol per minute) per gram of cellobiose. The enzyme may be added all at once, but it may also be added several times while monitoring the reaction by high performance liquid chromatography. The reaction may also be conducted by immobilizing the enzyme on an appropriate resin substrate such as an ion-exchange resin or hydrophobic resin as an enzyme reactor. The reaction time of about 1-4 days will be sufficient, but completion point of the reaction may be determined while monitoring the reaction.

The ascorbic acid derivative in the composition produced at the completion of the reaction may be further purified if desired by ordinary separating means such as membrane separation, ion-exchange column chromatography, activated carbon column chromatography, liquid chromatography, silica gel column chromatography or the like. For example, as a strongly acidic cation-exchange resin, there may be appropriately used an alkali metal salt-type, alkaline earth metal salt-type or $H^+$-type of a sulfonated styrene-divinylbenzene crosslinked copolymer resin. Commercially available products include Dowex™ 50W ×8 (the Dow Chemical Company), Amberlite™ CG-120 (Rohm & Haas Co.) and Diaion™ SK104 (Mitsubishi Chemical Industries Co., Ltd.). The unreacted ascorbic acid and β-glucosyl group-containing compound separated by the chromatography may be used as starting materials in the next round of enzyme reaction.

In order to achieve higher product purity, purification may be performed by high performance liquid chromatography. Specifically, a pure product may be obtained by employing a combination of a sugar/organic acid analyzing column and a volatile acid such as acetic acid, trifluoroacetic acid, and the like, or a combination of an ODS column with sublimating ammonium formate, and a volatile ion-pair reagent di-n-butylamine acetate which is used to analyze acidic substances. Identification of the target substance may be accomplished by comparative analysis of the mass spectrum or nuclear magnetic resonance spectrum against chemically synthesized 2-O-(β-D-glucopyranosyl)ascorbic acid.

The 2-O-(β-D-glucopyranosyl)ascorbic acid may be used in the form of a salt suitable for foods, cosmetics or drugs. As examples of salts there may be mentioned inorganic or organic alkali salts, including sodium salts, potassium salts, calcium salts and amine salts. The 2-O-(β-D-glucopyranosyl) ascorbic acid may be substituted at a hydroxyl group with a leaving group that is easily degraded in the body. As such leaving groups there may be mentioned acetyl ($C_2$), propionyl ($C_3$), butyryl ($C_4$), octanoyl ($C_8$), palmitoyl ($C_{16}$) and stearoyl ($C_{18}$).

5) Activity of 2-O-(β-D-glucopyranosyl)ascorbic acid (1): Inhibition of Ultraviolet Irradiation Damage 2-O-(β-D-glucopyranosyl)ascorbic acid clearly exhibits a stronger effect of preventing cell death of human skin epidermal keratinocytes (HaCaT) induced by ultraviolet B (UVB) irradiation compared to ascorbic acid or 2-O-(α-D-glucopyranosyl)ascorbic acid at the same concentration.

It is known that with irradiation on a portion of hairless mouse skin with light near the wavelength spectrum of sunlight (290-400 nm), reduction of ascorbic acid (vitamin C) occurs most rapidly among the antioxidant factors in mouse skin (Photodermatol. Photoimmunol. Photomed., 10(5), 183, 1994). Also, skin inflammation induced by UVB irradiation of shaven guinea pig dorsal skin can be inhibited by external application of ascorbic acid or 2-O-(α-D-glucopyranosyl) ascorbic acid, with the effect of 2-O-(α-D-glucopyranosyl) ascorbic acid being greater (Fragrance Journal, Vol.25, No.3, p.55, 1997). Daily administration of 10% ascorbic acid aqueous solution to pig skin for a period from 3 days to a week has also been reported to alleviate ultraviolet ray damage (Br. J. Dermatol., 121, 247, 1992).

However, the effect of the 2-O-(β-D-glucopyranosyl) ascorbic acid of the invention against the skin inflammation which is induced by ultraviolet irradiation and other ultraviolet ray damage is greater than that of ascorbic acid or 2-O-(α-D-glucopyranosyl)ascorbic acid. As mentioned above, the reason for this is believed to be its superior migration into tissue and longer life compared to 2-O-(α-D-glucopyranosyl) ascorbic acid.

In respect of the intracellular ascorbic acid concentration in human skin epidermal keratinocytes, 2-O-(β-D-glucopyranosyl)ascorbic acid is also maintained at a higher concentration for the longest time. This high concentration maintenance of intracellular ascorbic acid by 2-O-(β-D-glucopyranosyl)ascorbic acid is attributed to its activity of protecting cells against UVB irradiation. It is also clear that 2-O-(β-D-glucopyranosyl)ascorbic acid functions as a provitamin C which is intracellularly converted to ascorbic acid.

Activity of 2-O-(β-D-glucopyranosyl)ascorbic acid (2): Prevention of Wrinkles and Sagging Examination of collagen synthesis by normal human dermal fibroblasts (NHDF) indicates increased activity of 2-O-(β-D-glucopyranosyl)ascorbic acid compared to 2-O-(α-D-glucopyranosyl)ascorbic acid or ascorbic acid. This is also believed to be due to the prolonged higher concentration of intracellular ascorbic acid. That is, the collagen synthesis-promoting effect of ascorbic acid is believed to occur even in skin-derived fibroblasts, functioning for regeneration and reconstruction of the skin. In fact, application of ascorbic 2-phosphate, as a stable form of ascorbic acid, to burn victims has been reported to promote healing without cicatrization (Lecture Summaries of the Japanese Cosmetic Science Society, p.50, 1998). On the other hand, ascorbic acid is also known to inhibit collagen-degrading enzymes, and enzymes that degrade elastin which is essential for skin elasticity (Bio-antioxidant Provitamin C, p.63, 1999, Fragrance Journal Co.). These data suggest an effect of 2-O-(β-D-glucopyranosyl)ascorbic acid against wrinkles and sagging.

Activity of 2-β-D-glucopyranosyl)ascorbic acid (3): Whitening

Based on the fact that ascorbic acid inhibits tyrosinases and thereby suppresses melanin synthesis and that human application of cream containing 2-O-(α-D-glucopyranosyl)ascorbic acid inhibits pigmentation caused by ultraviolet irradiation (Fragrance Journal, Vol.25, No.3, p.55, 1997), it is strongly suggested that 2-O-(β-D-glucopyranosyl)ascorbic acid will have a similar whitening effect, and stronger than that of 2-O-(α-D-glucopyranosyl)ascorbic acid.

Activity of 2-O-(β-D-glucopyranosyl)ascorbic acid (4): Dynamics with Oral Ingestion Upon oral ingestion of 2-O-(β-D-glucopyranosyl)ascorbic acid by rats, unconverted 2-O-(β-D-glucopyranosyl)ascorbic acid is detected in the blood, indicating that it is absorbed in unconverted form through the intestinal tract. On the other hand, as mentioned above, oral ingestion of 2-O-(α-D-glucopyranosyl)ascorbic acid by rats results in no detection of the unconverted form in the blood, and therefore upon absorption it is almost completely decomposed in the intestinal tract and exists in the blood as ascorbic acid (J. Pharmacobio-Dyn., 13, 688, 1990). That is, upon oral ingestion, 2-O-(α-D-glucopyranosyl)ascorbic acid is absorbed as ascorbic acid and is more likely to be rapidly degraded in the blood. On the other hand, 2-O-(β-D-glucopyranosyl)ascorbic acid exists in the blood even in its unconverted form and migrates unconverted into the tissue, so that it is more likely to be activated to ascorbic acid in the tissues and cells.

The above experimental results and observations clearly indicate that 2-O-(β-D-glucopyranosyl)ascorbic acid and compositions comprising it are an excellent form of provitamin C useful for protecting skin and maintaining healthy skin, and may be used in skin cosmetics and skin protectors or in foods, as a provitamin C permitting efficient migration of ascorbic acid into the body and tissues.

6) Composition comprising 2-O-(β-D-glucopyranosyl)ascorbic acid

When a composition comprising 2-O-(β-D-glucopyranosyl)ascorbic acid according to the invention is used as a skin cosmetic or skin protector, the amount thereof may be within a wide range with no particular restrictions, but will ordinarily be 0.1-30 wt % and preferably 0.5-10 wt % with respect to the total amount of the composition. In the form of a composition, it may be appropriately combined with other components commonly used in cosmetics, such as oil components, surfactants, ultraviolet absorbers, lower alcohols, preservatives, bacteriocidal agents, coloring agents, powders, aromas, water-soluble polymers, buffering agents and the like, so long as the effect of the invention is not impaired. Such compositions may be used not only as skin cosmetics but also as quasi drugs in the form of lotions, emulsions, creams, packs, soaps or other medicinal cosmetics, or as drugs in the form of lotions, emulsions, creams, ointments or other external skin applications.

When a composition comprising 2-O-(β-D-glucopyranosyl)ascorbic acid of the invention is used as a food, it may be applied in food products in the same manner as described in Japanese Patent No. 2832848 in regard to 2-O-(α-D-glucopyranosyl)ascorbic acid, to prepare vitamin C-fortified foods. To cite Japanese Patent No. 2832848 specifically, because of its compatibility with various substances of various flavors including acidic, salty, astringent, zesty, bitter, etc., and its high acid resistance and heat resistance, it may be utilized as a vitamin C-fortifier, flavor enhancer, acidic flavoring, quality improver, stabilizer, antioxidant or the like in various common food products and flavorings, for example, in various types of seasonings such as soy sauce, powdered soy sauce, salted bean paste, powdered salted bean paste, unrefined sake, salted meat, fish flour, mayonnaise, dressing, vinegar, sake/soy/vinegar sauce, powdered sushi vinegar, chinese seasoning, tempura broth, noodle broth, sauce, ketchup, roast meat gravy, curry powder, stew seasoning, soup seasoning, stock seasoning, mixed condiment, sweet sake, low-alcohol sweet sake, table sugar and coffee sugar; Japanese sweets such as rice crackers, rice-cake cubes, millet/rice cake, fried dough cake, starch paste, rice cakes, bean-jam filled buns, sweet rice jelly, bean jelly, sweet bean paste, soft sweet bean paste, sweet balls, jelly, castella sponge cake and toffee; confectioneries such as bread, biscuits, crackers, cookies, pies, pudding, cream puffs, waffles, sponge cake, donuts, chocolate, chewing gum, caramel and candy; frozen desserts such as ice cream and sherbet; syrups such as fruit syrup and frozen nectar; spreads and pastes such as butter cream, custard cream, flower paste, peanut paste and fruit paste; processed fruit or vegetable products such as jams, marmalades, syrups and sweetened fruits; processed grain products such as bread, noodles, rice products and artificial meat products; fat and oil products such as salad oils and margarine; pickles such as pickled sliced vegetables, fresh radish pickles, pickled turnips and pickled scallions; pickle stock such as pickled radish stock and pickled cabbage stock; livestock products such as ham and sausage; fish meat products such as fish ham, fish sausage, boiled fish paste, pounded fish cake and sea urchin egg paste; delicacies such as salted cuttlefish or squid gut, vinegar-soaked tangle, dried cuttlefish strips and sundried blowfish; soy-boiled vegetables or fish made from layer, edible wild plants, dried cuttlefish, small fish or shellfish; vegetable foods such as boiled beans, potato salad, tangle rolls and tempura; dairy products such as cooked eggs, milk beverages, butter and cheese; bottled or canned fish meat, livestock meat, fruits and vegetables; liquor such as synthetic sake, flavored sake, fruit wine and western alcohol beverages; soft drinks such as coffee, cocoa, juice, carbonated beverages, lactic acid beverages and lactic acid bacteria beverages; and various instant products such as pudding mixes, hotcake mixes, juice mixes, coffee mixes, red-bean soup mixes, soup mixes and the like. It may also be conveniently used as a vitamin C-fortifier, flavor enhancer, antioxidant, taste improver or the like in feed or fodder for breeding animals such as livestock, poultry, bees, silkworms, fish and the like.

Effect of the Invention

The present invention provides the novel substance 2-O-(β-D-glucopyranosyl)ascorbic acid, which has physiological action superior to that of 2-O-(α-D-glucopyranosyl)ascorbic acid and is expected to have applications in the fields of cosmetics, quasi drugs, medicines and foods, as well as 2-O-(tetra-O-acetyl-β-D-glucopyranosyl)ascorbic acid as a novel intermediate thereof, a process for production of 2-O-(β-D-glucopyranosyl)ascorbic acid using the intermediate and a process for production of 2-O-(β-D-glucopyranosyl)ascorbic acid-comprising compositions by extraction and purification from a plant of *Lycium* genuse, and compositions comprising 2-O-(β-D-glucopyranosyl)ascorbic acid derived from a plant of *Lycium* genuse.

The invention further provides compositions comprising 2-O-(β-D-glucopyranosyl)ascorbic acid or 6-O-(β-D-glucopyranosyl)ascorbic acid obtained by glycosyltransferase reaction. It still further provides a method for easy removal of contaminants from solutions containing 2-O-(β-D-glucopyranosyl)ascorbic acid and industrial mass production of products with higher contents and higher purity of 2-O-(β-D-glucopyranosyl)ascorbic acid.

EXAMPLES

The present invention will now be explained in greater detail through examples, with the implicit understanding that the scope of the invention is in no way limited by these examples.

Example 1

Synthesis of 2-O-(2,3,4,6-tetra-O-acetyl-β-D-glucopyranosyl)ascorbic acid

After dissolving 5,6-O-isopropylideneascorbic acid (2 g, 9.3 mmol) in DMSO (20 ml), potassium carbonate (1.3 g, 9.4 mmol) and benzyl bromide (1.1 ml, 9.3 mmol) were added and the mixture was stirred at 50° C. for 4 hours. Water was added to the reaction solution which was then acidified with 1N HCl, extracted with ethyl acetate, washed with water and then with saturated saline, dried with anhydrous MgSO$_4$, concentrated under reduced pressure and purified by silica gel chromatography (AcOEt/n-hexane=3:1) to obtain 1.1 g of 3-O-benzyl-5,6-O-isopropylideneascorbic acid (39% yield).

A mixture of this benzyl derivative (0.6 g, 2.0 mmol) and 2,3,4,6-tetra-O-acetyl-1-O-(2,2,2-trichloroethoxycarbonyl)-β-D-glucopyranose (2.1 g, 4.0 mmol) was heated at 120-130° C. to melting. After 3 hours of reaction, the reaction solution was purified by column chromatography (gradient from 25%-50% AcOEt/n-hexane) to obtain 850 mg of 2-O-(2,3,4,6-tetra-O-acetyl-β-D-glucopyranosyl)-3-O-benzyl-5,6-o-isopropylideneascorbic acid (67% yield).

This glucoside (850 mg, 1.3 mmol) was dissolved in ethyl acetate (40 ml), and 10% Pd-C (200 mg) was added for hydrogenolysis. After 2 hours, the catalyst was filtered out and the filtrate was concentrated to yield approximately 750 mg of 2-O-(2,3,4,6-tetra-O-acetyl-β-D-glucopyranosyl)-5,6-O-isopropylideneascorbic acid.

The debenzylated compound (500 mg, 0.9 mmol) was dissolved in acetic acid (5 ml), water (5 ml) was added, and the mixture was heated at 50-60° C. for 1.5 hours while stirring. After concentrating the reaction solution, the obtained residue was extracted with ethyl acetate, washed with water and then with saturated saline, dried with anhydrous $MgSO_4$ and concentrated under reduced pressure, and then the obtained residue was recrystallized from ethyl acetate/hexane to obtain 320 mg of 2-O-(2,3,4,6-tetra-O-acetyl-β-D-glucopyranosyl)ascorbic acid (48% yield).

$^1$H-NMR (δ ppm, DMSO-$d_6$); 1.94-2.01(12H), 3.42(3H, m), 3.7-4.3(4H, m), 4.7-5.1(4H, m), 5.3-5.4(2H, m), 12.00 (1H, br). FABMS(+) m/z: 507.

Example 2

Synthesis of 2-O-(β-D-glucopyranosyl)ascorbic acid

After dissolving 2-O-(2,3,4,6-tetra-O-acetyl-β-D-glucopyranosyl)ascorbic acid (300 mg, 0.6 mmol) in methanol (10 ml), a solution of potassium carbonate (600 mg) in water (9 ml) was added and the mixture was stirred for 30 minutes. The reaction solution was neutralized with IR-120($H^+$), the resin was filtered off, and washing was performed with methanol and a 50% methanol aqueous solution. The filtrate and washing solution were combined and concentrated, and then water was added and the mixture was lyophilized to obtain 2-O-(β-D-glucopyranosyl)ascorbic acid as amorphous crystals (190 mg, 100% yield).

$^1$H-NMR (δ ppm, $D_2O$); 3.1-3.3(4H, m), 3.4-3.5(3H, m), 3.58(1H, d), 3.80 (1H, t), 4.61(1H, d), 4.66(1H, d). FABMS (−) m/z: 337.

Example 3

Measurement of 2-O-(β-D-glucopyranosyl)ascorbic acid Content of a Plant of Lycium genuse Extracts obtained by immersing 3 g of different dry plants in a 10-fold volume of 70% ethanol at room temperature for 7 days were diluted 10-fold with 1.5% metaphosphoric acid/5 M KOH (pH 3.5) and used as test samples for identification of naturally occurring 2-O-(β-D-glucopyranosyl)ascorbic acid, based on the retention time of 2.63 minutes in high performance liquid chromatography of chemically synthesized 2-O-(β-D-glucopyranosyl)ascorbic acid (LC-10Ai System by Shimadzu Co., Ltd.; column: Inertsil ODS-3 (GL Science Co., Ltd., 4.6×150 mm, 5 μm), mobile phase: 20% MeOH-20 mM phosphate-5 mM tetra-n-amylammonium bromide, flow rate: 1.0 mL/min, column temperature: 35° C., detection wavelength: 254 nm). As a result, a peak corresponding to 2-O-(β-D-glucopyranosyl)ascorbic acid was found in extracts of *lycii fructus* from Neimonggol *Lycium barbarum* L., Ningxia *Lycium barbarum* L. and Hebei *Lycium Chinense* Mill. The same was found in a sample similarly prepared by adding a 2-fold amount of 70% ethanol to 100 g of fresh fruit of Ningxia *Lycium barbarum* L. Each solid extract was measured by lyophilization and weight measurement after concentration of 5 mL of the liquid extract under reduced pressure. Taking into account the calibration curves obtained using the solid extracts and chemically synthesized product, the concentrations of the extracts and the degree of dilution, the contents of the extracts were determined to be from 0.86% to 1.2%.

Example 4

Purification of 2-O-(β-D-glucopyranosyl)ascorbic acid in *Lycii fructus*

After pulverizing 100 g of Ningxia *Lycium barbarum* L. with a Model TS-10M tablet pulverizer by Tosho Co., Ltd., 800 mL of 30% ethanol was added for immersion at room temperature for 6 days, followed by filtration, concentration under reduced pressure and lyophilization to obtain 65.7 g of product. A 1.94 g portion of the extract (2-O-(β-D-glucopyranosyl)ascorbic acid content: 0.86%) was dissolved in distilled water to make 40 mL (pH 4.5, electric conductivity: 1.7 mS/cm). The sample was passed through a Dowex 1-X8 column (acetate form, 1.5×12 cm) at SV=1. It was then washed with an approximately 10 column volume (200 mL) of distilled water, subjected to linear gradient elution (100 mL×2) with 0-0.1 M acetic acid, subjected to linear gradient elution (100 mL×2) with 0.1-1.0 M acetic acid, and then eluted with 1.0 M acetic acid. The absorbance at 280 nm was measured and the elution of the 2-O-(β-D-glucopyranosyl) ascorbic acid was examined by high performance liquid chromatography in comparison with the retention time of the chemically synthesized product. The apparatus and column temperature were the same as in Example 1, but the other conditions were changed to the following. Column: Inertsil ODS-3 (GL Science Co., Ltd., 3.0×150 mm, 5 μm), flow rate: 0.3 mL/min, detection wavelength: 245 nm, mobile phase: 2% MeOH-0.2 M $KH_2PO_4/H_3PO_4$ (pH 3.0)-0.2 mM EDTA-0.5 mM dodecyltrimethylammonium chloride. The retention time of the chemically synthesized product 2-O-(β-D-glucopyranosyl)ascorbic acid under these conditions was 6.5 minutes. As a result of examination by high performance liquid chromatography, the substance adsorbed to the column was found to have eluted in fractions 19-25 with 0.1-1.0 M acetic acid linear elution (26 mg, 78% total yield for fractions 19-25, 50% purity). The results are shown in FIG. 1.

A portion of the fractions 19-25 corresponding to 2-O-(β-D-glucopyranosyl)ascorbic acid was supplied to high performance liquid chromatography to obtain a high purity product. The conditions were as follows. LC System by Gilson Co. (Type 305 Master Pump, Type 116 UV detector), column: ODS-UG-5 (4.6×250 mm, 5 μm, product of Nomura Chemical Co., Ltd.), mobile phase: 5% methanol/20 mM ammonium formate/5 mM di-n-butylamine acetate, flow rate: 0.5 mL/min, detection wavelength: 254 nm, fractionation at 0.5 min increments using an FC-203 Type B Fraction Collector (Gilson Co.). The corresponding fraction was concentrated under reduced pressure and lyophilized, dissolved in Deuterium Oxide and its nuclear magnetic resonance spectrum measured and compared with the synthesized product. The results are shown in FIG. 2.

Example 5

Enzyme synthesis of
2-O-(β-D-glucopyranosyl)ascorbic acid

Commercially available cellulase, β-glucosidase and β-glucanase enzyme agents were examined based on the retention time of 5.2 minutes for chemically synthesized 2-O-(β-D-glucopyranosyl)ascorbic acid in a LC System by Gilson Co. (Type 305 Master Pump, Type 116 UV detector), column: Inertsil ODS-3 (DL Science Co., Ltd., 4.6×150 mm, 5 μm), mobile phase: 20% MeOH-20 mM phosphate-5 mM tetra-n-amylammonium bromide, flow rate: 0.5 ml/min, detection wavelength: 254 nm). The enzyme reaction system was dissolved with 10 mM acetate buffer (pH 5.0) to 1 ml, for 0.3 M cellobiose and 0.2 M ascorbic acid. A 50 μl portion of the enzyme solution was then added thereto and reaction was initiated at 37° C. After heating at 100° C. for 5 minutes to terminate the reaction, the produced β-D-glucopyranosylascorbic acid was analyzed by high performance liquid chromatography. As a result, β-transglucosylation activity was found in the cellulase (Sigma), β-glucosidase (Toyobo, Nacalai Tesque), Cellulosin T2 (Hankyu Kyoei Bussan), cellulase "Onozuka" RS, "Onozuka" FA and Pancelase BR (Yakult Pharmaceutical Ind. Co., Ltd.). Free ascorbic acid appeared at the position of 4.0 minutes, but peaks were also observed at adjacent positions of 3.6 minutes and 5.2 minutes, and these were designated as substance X and substance Y, respectively. The transglucosylation ratio for substance X was 15.7% and that for substance Y was 0.8%. When substances X and Y were subjected to co-chromatography with chemically synthesized product, substance X matched the holding time for 6-O-(β-D-glucopyranosyl)ascorbic acid and substance Y for 2-O-(β-D-glucopyranosyl)ascorbic acid.

After removing the contaminating protein by using a UF membrane with cutting molecular weight of 10,000, the free ascorbic acid was removed by fractionation using high performance liquid chromatography [LC System by Gilson Co. (Type 305 Master Pump, Type 116 UV detector), column: SUGAR SH1011 (Showa Denko Co., Ltd.), mobile phase: 0.1 M acetic acid, flow rate: 0.5 mL/min, column temperature: 30° C., detection: differential refractometer, 0.25 ml fractionation]. The fractions containing substance X and substance Y eluted at 29-31, and a 24.7 μg sample was obtained at a 96% yield.

This was then supplied to high performance liquid chromatography to obtain a high purity product. The conditions were as follows. LC System by Gilson Co. (Type 305 Master Pump, Type 116 UV detector), column: ODS-UG-5 (4.6×250 mm, 5 μm, product of Nomura Chemical Co., Ltd.), mobile phase: 5% methanol/20 mM ammonium formate/5 mM di-n-butylamine acetate, flow rate: 0.5 mL/min, detection wavelength: 254 nm, fractionation at 0.5 min increments using an FC-203 Type B Fraction Collector (Gilson Co.). The fractions corresponding to substance X and substance Y were concentrated under reduced pressure, lyophilized and dissolved in Deuterium Oxide, and the nuclear magnetic resonance spectrum was measured and compared with chemically synthesized 2-O-(β-D-glucopyranosyl)ascorbic acid. In the HSQC spectrum, the chemical shifts of the 4-position, 5-position and 6-position carbons of the ascorbic acid moiety of the chemically synthesized product were 73, 73 and 66 ppm, respectively, while for substance X the chemical shifts of the 4-position, 5-position and 6-position were all 73 ppm and thus a shift towards lower magnetic field was seen only for the 6-position carbon. Substance X was therefore concluded to be 6-O-(β-D-glucopyranosyl)ascorbic acid.

Figure 3:
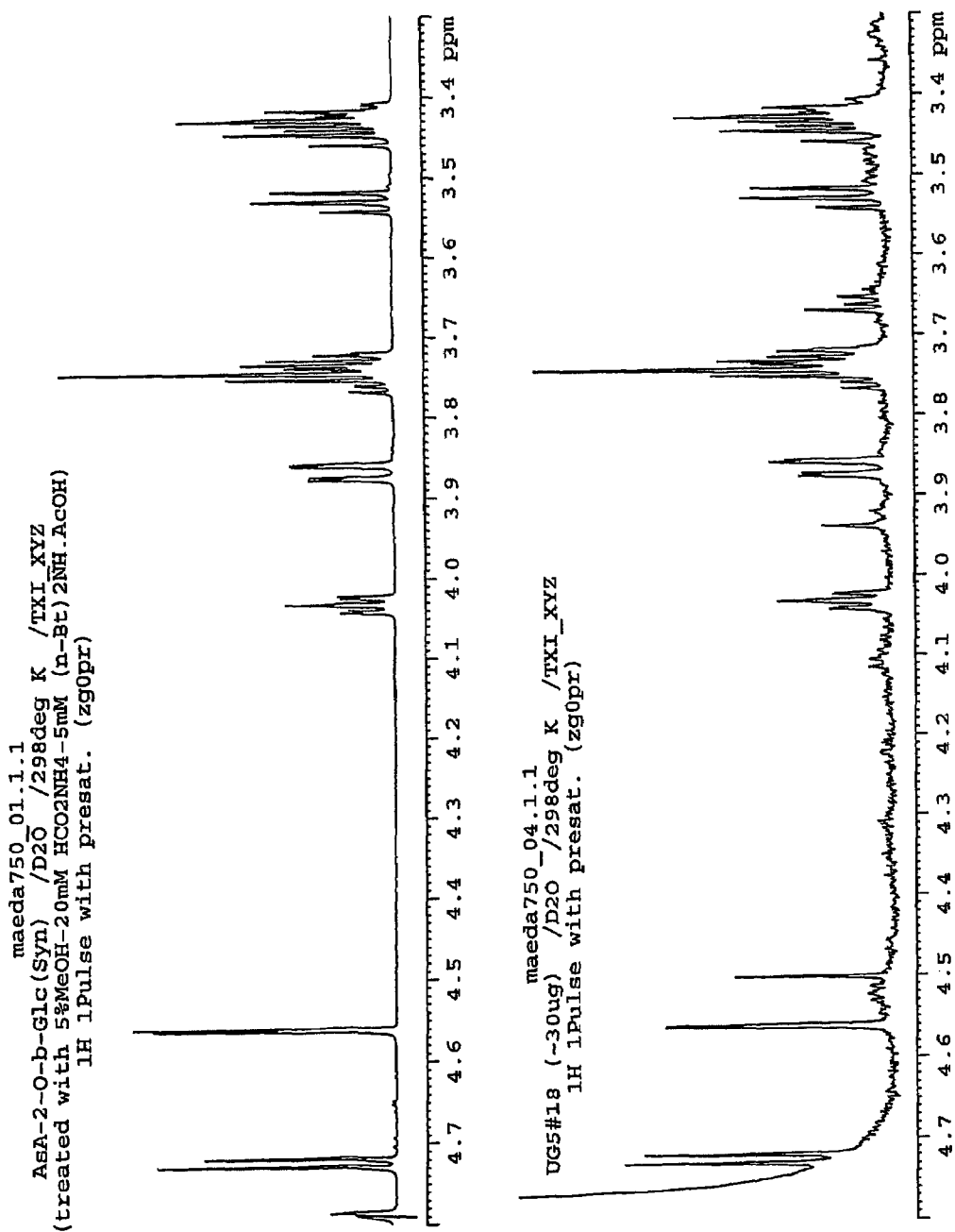
FIG. 3 shows the results of comparing enzymatically synthesized 2-O-(β-D-glucopyranosyl)ascorbic acid (substance Y) with a chemically synthesized product based on $^1$H-NMR. The upper chart is the spectrum for chemically synthesized 2-O-(β-D-glucopyranosyl)ascorbic acid, and the lower chart is the spectrum for the enzymatic reaction product 2-O-(β-D-glucopyranosyl)ascorbic acid (substance Y).
Figure 4:
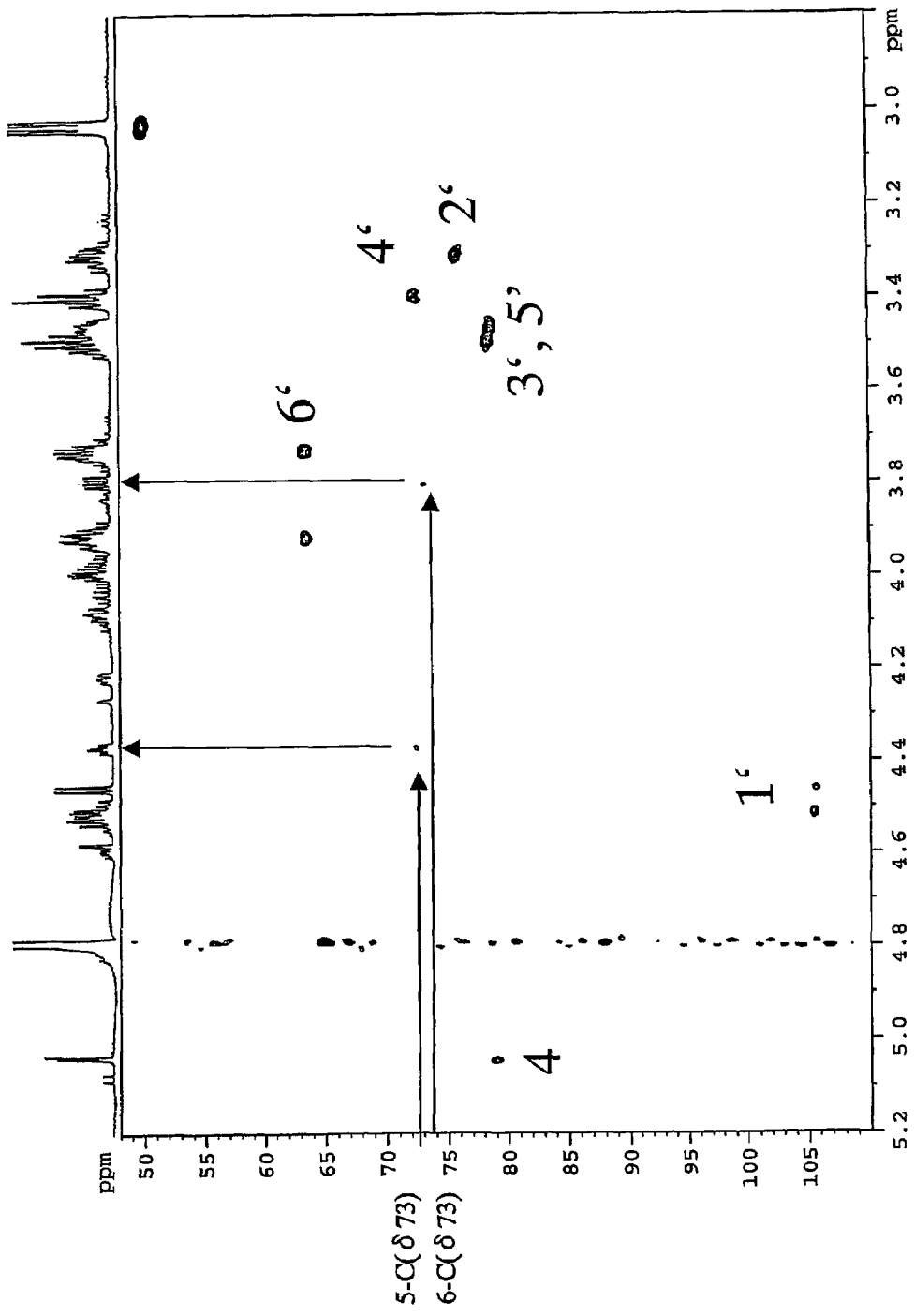
FIG. 4 shows the HSQC spectrum for enzymatically synthesized 6-O-(β-D-glucopyranosyl)ascorbic acid (substance X), in comparison with chemically synthesized 2-O-(β-D-glucopyranosyl)ascorbic acid. The upper chart is the spectrum for the enzyme reaction product 6-O-(β-D-glucopyranosyl)ascorbic acid (substance X), and the lower chart is the spectrum for chemically synthesized 2-O-(β-D-glucopyranosyl)ascorbic acid.

Substance Y matched in the comparison with one dimentional NMR spectrum of chemically synthesized 2-O-(β-D-glucopyranosyl)ascorbic acid, and was therefore concluded to be 2-O-(β-D-glucopyranosyl)ascorbic acid. The results are shown in FIG. 3 and FIG. 4.

Example 6

Transferase Reaction Conditions

1) Ammonium Sulfate Fractionation

Cellulase agent (Sigma) was dissolved in 20 mM acetate buffer (pH 5.0) to a concentration of 4%, and ammonium sulfate solutions at 20% graded saturations were successively added to prepare 0-20%, 20-40%, 40-60% and 60-80% saturated ammonium sulfate precipitation fractions. After dissolving each of the fractions in 20 mM acetate buffer (pH 5.0), the transfer product was confirmed according to Example 5. As a result, transfer activity was found in the ammonium sulfate 20-40% saturated fraction.

2) Effect of pH

The test substance was dissolved to 1 ml with 0.1 M acetate buffer adjusted to various pH levels, for concentrations of 0.3 M cellobiose and 0.2 M free ascorbic acid. A 50 μl portion of enzyme solution was added thereto for reaction at 37° C. for 40 hours. After the reaction, the (β-D-glucopyranosyl)ascorbic acid produced was analyzed by high performance liquid chromatography.

The results are shown in Table 1. The transglucosylation products were found at pH 3 or at a higher pH, and 2-O-(β-D-glucopyranosyl)ascorbic acid was produced at 0.8% in reaction at pH 5 and at 1.0% in reaction at pH 6. Also, 6-O-(β-D-glucopyranosyl)ascorbic acid was produced at 11.8% in reaction at pH 5 and at 11.2% in reaction at pH 6.

TABLE 1

| pH | AA (%) | AA6βG (%) | AA2βG (%) |
| --- | --- | --- | --- |
| 2 | 99.3 | 0.7 | 0 |
| 3 | 93.5 | 6.2 | 0.3 |
| 4 | 87.9 | 11.6 | 0.5 |
| 5 | 87.4 | 11.8 | 0.8 |
| 6 | 87.8 | 11.2 | 1.0 |

3) Reaction with Ascorbic Acid Derivatives

The test substance was dissolved to 1 ml with 0.1 M acetate buffer adjusted to various pH levels, for concentrations of 0.3 M cellobiose and 0.2 M each of free ascorbic acid, sodium ascorbate, calcium ascorbate, free isoascorbic acid and sodium isoascorbate. A 50 μl portion of enzyme solution was added thereto for reaction at 37° C. for 20 hours, after which the (β-D-glucopyranosyl)ascorbic acid was analyzed in the same manner as described above. The results are shown in Table 2. Each ascorbic acid derivative acted as a transfer reaction acceptor, with each producing a 2-O-(β-D-glucopyranosyl) derivative.

TABLE 2

|  | AA (%) | AA6βG (%) | AA2βG (%) |
| --- | --- | --- | --- |
| Free ascorbic acid | 91.2 | 7.9 | 0.9 |
| Sodium ascorbate | 97.6 | 1.6 | 0.8 |
| Calcium ascorbate | 95.9 | 2.8 | 1.3 |
| Free isoascorbic acid | 95.4 | 3.8 | 0.8 |
| Sodium isoascorbate | 98.4 | 0.8 | 0.8 |

4) Partial Purification

Cellulase agent (Sigma), Cellulase "Onozuka" RS and Pancelase BR (Yakult Pharmaceutical Ind. Co., Ltd.) were each applied to Q-Sepharose ion-exchange resin (Amersham Pharmacia Biotech Co.) equilibrated with 20 mM acetate buffer (pH 5.0) after ammonium sulfate precipitation of the enzyme protein, and all of the transfer activity was found in the flow-through fractions. The results are shown in Table 3.

TABLE 3

|  | AA (%) | AA6βG (%) | AA2βG (%) |
| --- | --- | --- | --- |
| Cellulase (Sigma) | 89.9 | 9.0 | 1.1 |
| Onozuka RS (Yakult) | 86.4 | 11.6 | 2.0 |
| Pancelase BR (Yakult) | 94.0 | 5.4 | 0.6 |

5) Enzyme Immobilization

The enzyme agent Pancelase BR sold as a food additive contains, in addition to the enzyme (5%), lactose at 95%. After adding 6 g of Pancelase BR enzyme agent to 60 ml of 20 mM acetate buffer (pH 5.0), the mixture was applied to Marathon WBA (2 ml resin, product of Dow Chemical Co.) equilibrated with the same buffer, and the flow-through fraction was obtained. Ammonium sulfate was then added to 20% saturation, and the mixture was immobilized on Chitopearl BCW3510 (2 ml resin, product of Fuji Spinning Co., Ltd.) equilibrated with 20% saturated ammonium sulfate/20 mM acetate buffer (pH 5.0), to prepare the immobilized enzyme. The immobilized enzyme resin was added to 10 ml of 20% saturated ammonium sulfate/20 mM acetate buffer (pH 5.0) dissolving 0.35 g of ascorbic acid and 1 g of cellobiose, and reacted at 37° C. The results are shown in Table 4.

TABLE 4

| Reaction time | AA (%) | AA6βG (%) | AA2βG (%) |
| --- | --- | --- | --- |
| Day 1 | 94.1 | 4.8 | 1.1 |
| Day 2 | 91.2 | 7.6 | 1.2 |

Example 7

Purification of (β-D-glucopyranosyl)ascorbic acid

A 20 mg portion of Cellulase agent (Sigma) was dissolved in 1 ml of 20 mM acetate buffer (pH 5.0), the mixture was applied to Marathon WBA (0.5 ml resin, product of Dow Chemical Co.) equilibrated with the same buffer, and the flow-through fraction was obtained. The enzyme solution was added to 10 ml of 20 mM acetate buffer (pH 5.0) which had dissolved 0.35 g of ascorbic acid and 1 g of cellobiose, and the mixture was reacted at 37° C. for 2 days to obtain a reaction solution containing 11.8% 6-O-(β-D-glucopyranosyl)ascorbic acid and 0.8% 2-O-(β-D-glucopyranosyl)ascorbic acid. The solution was filtered with a UF membrane to collect and remove the enzyme, and the resulting solution (pH 4.3, electric conductivity: 1.6 mS/cm) was passed through a Dowex 1-X8 column (acetate form, 1.5×12 cm) at SV=2.5. It was then washed with an approximately 10 column volume (200 mL) of distilled water and subjected to linear gradient elution (80 mL×2) with 0-0.1 M acetic acid and to linear gradient elution (80 mL×2) with 0.1-1.0 M acetic acid. The fractionation successively produced high 6-O-(β-D-glucopyranosyl)ascorbic acid content fractions (fractions 65-68), a high unreacted ascorbic acid content fraction and high 2-O-(β-D-glucopyranosyl)ascorbic acid content fractions (fractions 101-108). Fractions 101-108 were collected as the high 2-O-(β-D-glucopyranosyl)ascorbic acid content fractions (2.4 mg, 45% yield).

Example 8

Figure 5:
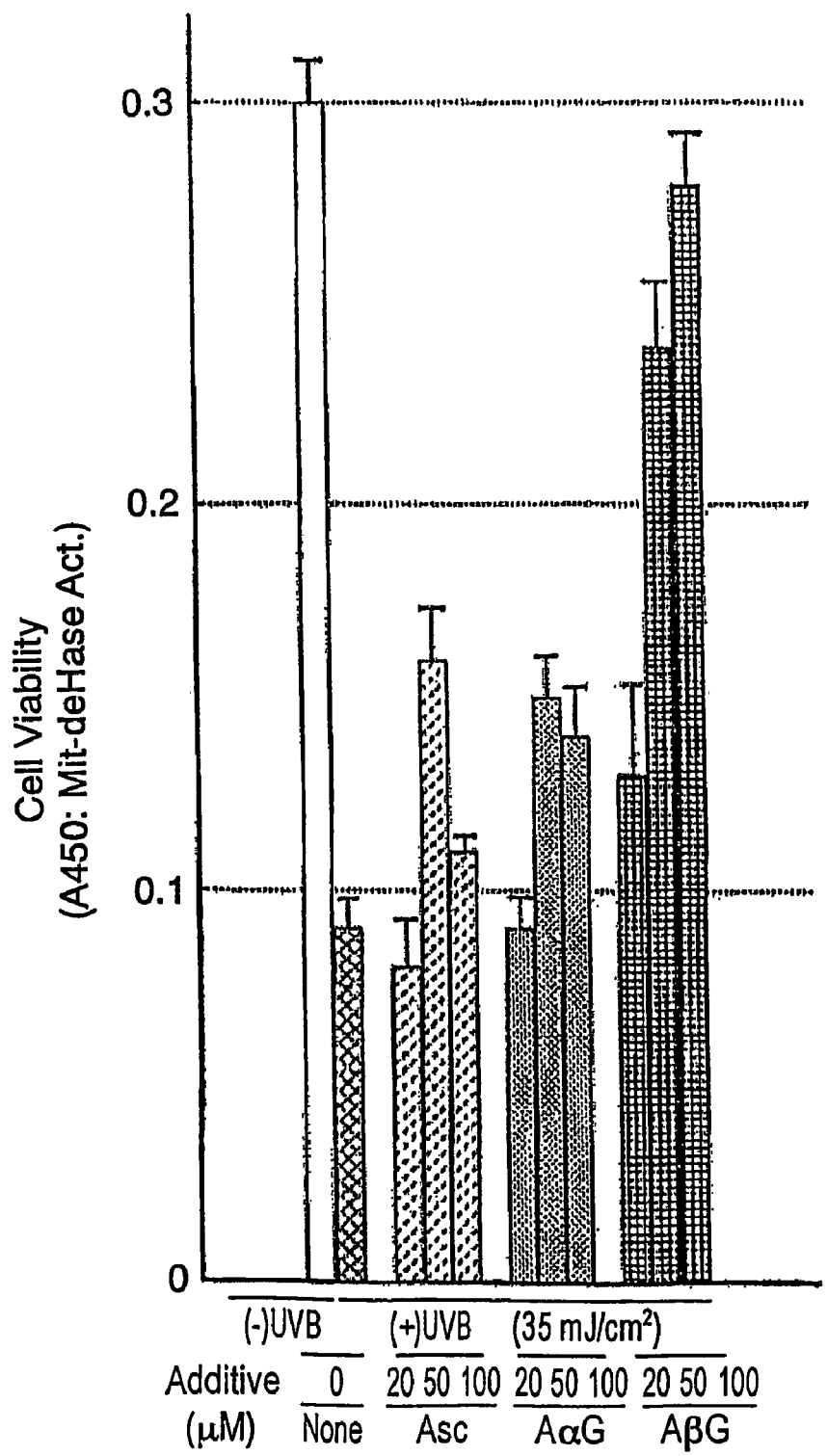
FIG. 5 shows the protective effect of previous administration with 2-O-(β-D-glucopyranosyl)ascorbic acid against cell death of human skin epidermal keratinocytes (HaCaT) induced by ultraviolet B (UVB) irradiation.

Protecting Effect of 2-O-(β-D-glucopyranosyl)ascorbic Acid Against Cell Death of Human Skin Epidermal Keratinocytes (HaCaT) Induced by Ultraviolet B (UVB) Irradiation The human skin epidermal keratinocyte line HaCaT (a cell line provided by Professor Fusenig of Heidelberg University) was plated on a 24-well plate at 10,000 cells/well with Dulbecco's modified Eagle medium (DMEM) containing 10% fetal bovine serum (FBS) and after 18 hours, the cells were irradiated with UVB (maximum wavelength: 312 nm) at 35 millijoules/square centimeter ($mJ/cm^2$). Two hours before irradiation, 2-O-(β-D-glucopyranosyl)ascorbic acid was added at 20-100 μM and removed with rinsing just before irradiation. The irradiation was performed in PBS in the absence of chemical agents, after which culturing was continued in DMEM containing 10% FBS, and the viable cell count was determined 24 hours after irradiation by measuring the mitochondrial dehydrogenase activity using 2-(4-iodophenyl)-3-(4-nitrophenyl)-5-(2,4-disulfophenyl)-2H-tetrazolium monosodium salt (WST-1). The results are shown in FIG. 5. For comparison, 2-O-(α-D-glucopyranosyl)ascorbic acid and ascorbic acid were examined in a similar manner, and the results are also shown in FIG. 5.

Example 9

Figure 6:
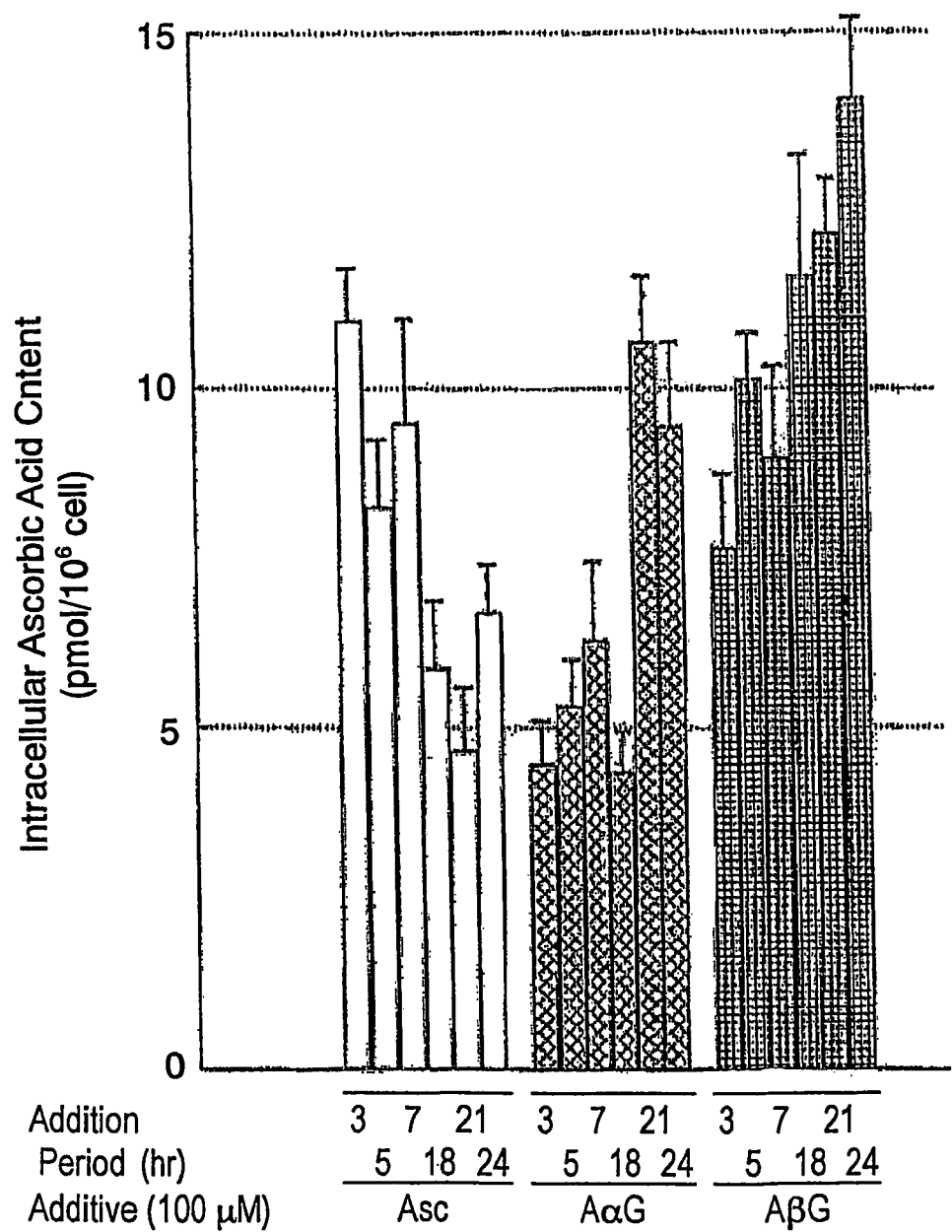
FIG. 6 shows the effect of 2-O-(β-D-glucopyranosyl)ascorbic acid on intracellular ascorbic acid concentration in human skin epidermal keratinocytes.

Effect of 2-O-(β-D-glucopyranosyl)ascorbic acid on Intracellular Ascorbic Acid Concentrations in Human Skin Epidermal Keratinocytes Human skin epidermal keratinocyte cells HaCaT were plated onto a 100 mm diameter dish at a cell count of 370,000. After 16 hours of culturing, there was added 100 μM of 2-O-(β-D-glucopyranosyl)ascorbic acid dissolved in DMEM containing 10% FBS and 40% of 24-hour serum-free HaCaT culture solution. The medium was removed 3-24 hours after the addition, rinsing was performed twice with ice-cooled PBS, and the cell sheet was treated with trypsin to obtain the separated cells. These were suspended in PBS containing 50 μM dithiothreitol (DTT) and rinsed 3 times by centrifugation. The cells received freeze-thawing twice were crushed with a Potter-type teflon homogenizer for 30 sec on the ice. The cell homogenate was centrifuged at 5° C., and supernate thus separated was stored on the ice. The supernatant was subjected to treatment with Molcut (product of Nihon Millipore Co., Ltd.; High-pressure ultrafiltration unit, nominal molecular weight limit (NMWL): 10,000, polyethersulfone membrane), and the amount of intracellular ascorbic acid was analyzed by high performance liquid chromatography (AS-8020 System by Toso Co., Ltd., column: Shodex ODSpak (4.6×150 mm, product of Showa Denko Co., Ltd.), mobile phase: 0.1 M $KH_2PO_4$—$H_3PO_4$ (pH 2.35)-0.1 mM EDTA-2 Na, flow rate: 1.5 mL/min) using a coulometric electrochemical detector (ESA Co., Bedford, Mass., 200 mV). The results are shown in FIG. 6. For comparison, 2-O-(α-D-glucopyranosyl)ascorbic acid and ascorbic acid were examined in a similar manner, and the results are also shown in FIG. 6.

Example 10

Promoting Effect of 2-O-(β-D-glucopyranosyl)ascorbic acid on Collagen Synthesis by Normal Human Dermal Fibroblasts (NHDF)

Figure 7:
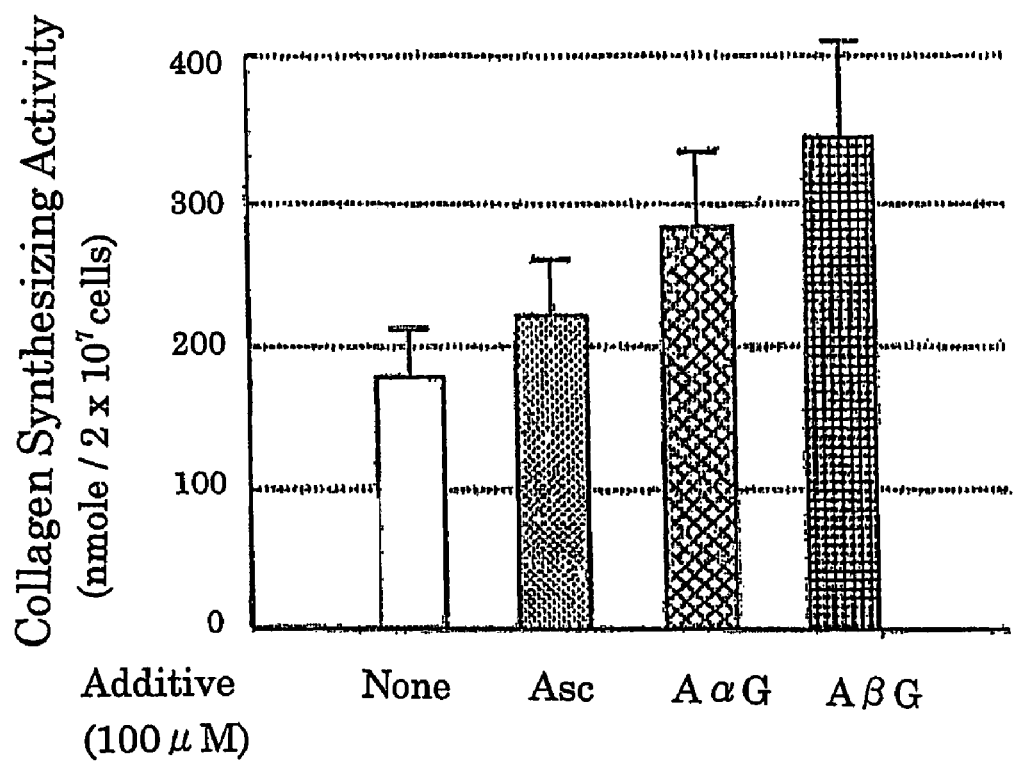
FIG. 7 shows the promoting effect of 2-O-(β-D-glucopyranosyl)ascorbic acid on collagen synthesis by normal human dermal fibroblasts (NHDF).

Normal human dermal fibroblast cells (NHDF) were plated onto a 100 mm diameter dish at a cell count of 370,000. After 16 hours of culture, there was added 100 μM of 2-O-(β-D-glucopyranosyl)ascorbic acid dissolved in DMEM medium containing 10% FBS and 40% of 24-hour serum-free NHDF culture solution. After another hour, 0.12 mL (120 μCi) of L-[2,3-$^3$H]proline was added and culturing was continued for 48 hours. The medium was removed after culturing, and the cell sheet was rinsed 4 times with PBS. The cells were then treated with trypsin, lysed with an alkali, and then neutralized to obtain the intracellular protein. The fraction obtained by digesting this protein with *Clostridium* collagenase was measured in terms of radioactivity with a liquid scintillation counter using Scintisol EX-H. The intracellular protein fraction not treated with collagenase was also measured in terms of radioactivity using a liquid scintillation counter. The difference in radioactivities was calculated and recorded as the collagen synthesizing activity. The results are shown in FIG. 7. For comparison, 2-O-(α-D-glucopyranosyl)ascorbic acid and ascorbic acid were examined in a similar manner, and the results are also shown in FIG. 7.

Example 11

Intestinal Absorption of 2-O-(β-D-glucopyranosyl)ascorbic acid in Rat

Figure 8:
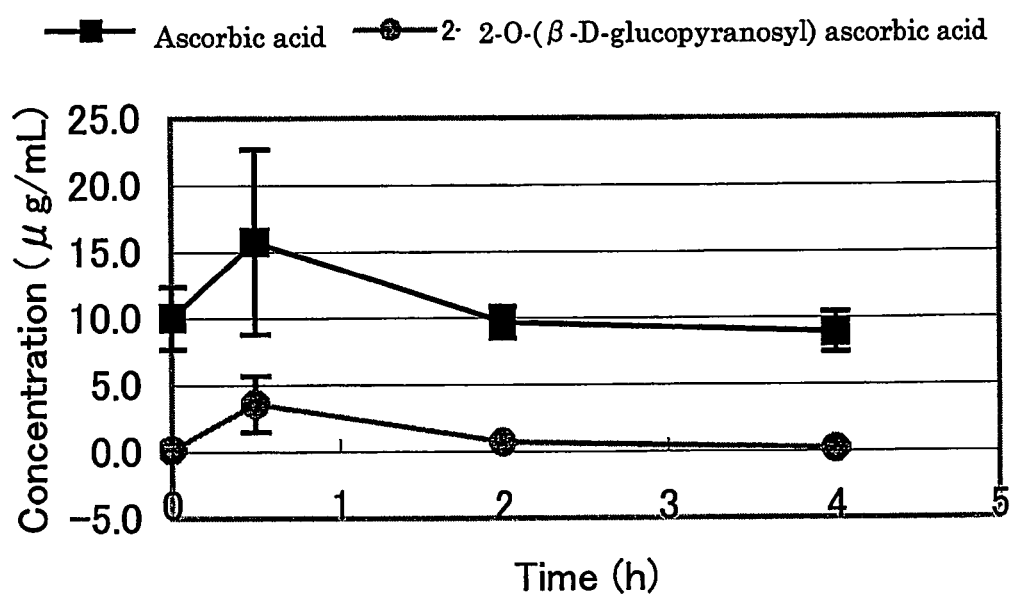
FIG. 8 shows the rat portal blood and plasma concentrations after oral administration of 2-O-(β-D-glucopyranosyl)ascorbic acid at 100 mg/kg.

A solution of 2-O-(β-D-glucopyranosyl)ascorbic acid in Milli-Q Ultrapure Water (Millipore Corporation) (100 mg/4 mL) was orally administered at a dose of 100 mg/kg by using a feeding tube to overnight-starved and awake 10-week-old male Wistar rats (n=3) purchased from Nihon Charles River Co. After 0, 0.5, 2 and 4 hours, heparinized blood samples were collected from the portal vein and the plasma from each sample was separated by centrifugation (6000×g, 10 min). After addition of an equivalent of ice-cooled 10% metaphosphoric acid (containing 40 mM deferoxamine mesylate), the mixture was centrifuged (10,000×g, 10 min) to obtain protein-removed portal vein plasma, of which the unconverted 2-O-(β-D-glucopyranosyl)ascorbic acid and ascorbic acid concentrations were measured by high performance liquid chromatography (LC-10Ai System by Shimadzu Co., Ltd., Column: Inertsil ODS-3 (GL Science Co., Ltd., 3.0×150 mm, 5 μm), mobile phase: 15% MeOH-17 mM $KH_2PO_4/H_3PO_4$ (pH 3.5)-5 mM tetra-n-amylammonium bromide, flow rate: 0.3 mL/min, column temperature: 35° C., detection wavelength: 254 nm). The unconverted 2-O-(β-D-glucopyranosyl) ascorbic acid and the metabolite (ascorbic acid) were found present in maximum amounts 30 minutes after administration. The results are shown in FIG. 8.

These results demonstrated that the 2-O-(β-D-glucopyranosyl)ascorbic acid of the invention is a provitamin C with superior physiological effects from the standpoint of stability and prolonged activity, compared to 2-O-(α-D-glucopyranosyl)ascorbic acid. It is therefore expected to have applications in the fields of foods, cosmetics, and quasi drugs or drugs. In addition, 2-O-(tetra-O-acetyl-β-D-glucopyranosyl)ascorbic acid is a novel intermediate useful for production of 2-O-(β-D-glucopyranosyl)ascorbic acid. Compositions comprising 2-O-(β-D-glucopyranosyl)ascorbic acid can be obtained by extraction from a plant of *Lycium* genuse. In addition to chemical synthesis, 2-O-(β-D-glucopyranosyl)ascorbic acid can also be obtained by glycosyltransferase reaction.

Example 12

Effect of 2-O-(β-D-glucopyranosyl)ascorbic acid on Population Doubling (PDL) Level of Human Dermal Fibroblasts Normal human dermal fibroblast (NHDF) cells were plated onto a 100 mm diameter dish at a cell density of 370,000. After 16 hours of culture in DMEM supplied with 10% FBS, the medium was replaced by DMEM fortified with 10 % FBS and supplied with 40% of a domestic-conditioned medium containing 100 μM of 2-O-(β-D-glucopyranosyl)ascorbic acid. The cultivation was continued for 46-188 hours until cells reached a near confluent state. The domestic-conditioned medium was prepared by separately culturing NHDF cells to the state of near confluency, which was further cultivated in a serum-free medium for 24 hours, and collecting the culture supernatant, which was stored in a refrigerator and used within 3 days. In connection with the above 46-188 hours of cultivation, the medium was changed every 3 days with fresh DMEM fortified with 10% FBS and supplied with 40% of the domestic-conditioned medium containing 100 μM of 2-O-(β-D-glucopyranosyl)ascorbic acid. When medium change was made, the cell number in the old culture medium was counted and used in the PDL assessment. The number of cells adhering onto the plate was counted by Coulter counter. PDL value at the start of culture was taken as 0, and PDL values thereafter were calculated by the equation:

$$PDL = \log_2 (\text{recovered cell number/seeded cell number}).$$

Figure 9:
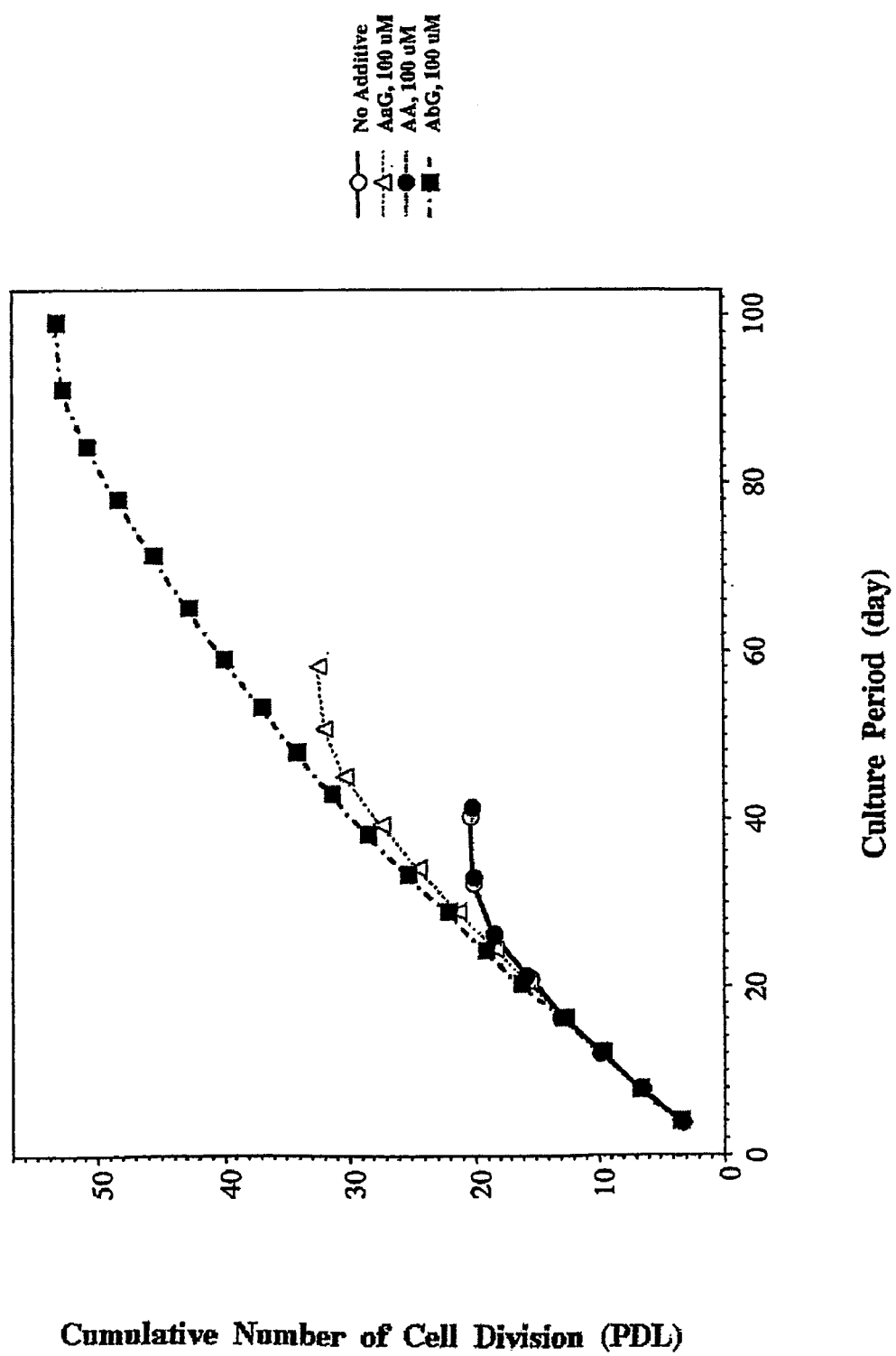
FIG. 9 shows the effect of 2-O-(β-D-glucopyranosyl)ascorbic acid on population doubling levels (PDLs) of normal human dermal fibroblast (NHDF) cells. 2-O-(β-D-Glucopyranosyl)ascorbic acid showed a remarkable life-supporting effect. Namely, while NHDF died of aging at PDL of 20.1 in the absence of ascorbic acid derivative, the PDL of NHDF was greater by 2.62 times in the presence of said ascorbic acid derivative. The results indicate that the lifelong cell-supplying ability of NHDF was made greater by $2^{2.62}$, and the ascorbic acid derivative of the invention will make a great contribution in protecting the skin from aging and compensating dead cells in the skin.

The results are shown in FIG. 9. For comparison, similar tests were conducted substituting 2-O-(α-D-glucopyranosyl) ascorbic acid and ascorbic acid for 2-O-(β-D-glucopyranosyl)ascorbic acid, and the results are also shown in FIG. 9.

Example 13

Effect of 2-O-(β-D-glucopyranosyl)ascorbic acid on the Reduction Speed of Telomere Lengths Genomic DNA extract from NHDF cells was treated with restriction enzymes which do not cleave telomere sequence, and a DNA fragment containing the entire length of telomere (Terminal Restriction Fragments, TRFs) was prepared. The TRFs were separated by electrophoresis and the length of the telomere DNA was quantified with a labeled probe specifically binding to telomere. Details of the method used in the study is described in Life Sciences, Vol.63, No.11, 935-948 (1998).

Preparation of TRF from NHDF Cells and Agarose Gel Electrophoresis

The fibroblast cells (NHDF) from human skin epidermis were dispersed by treatment with trypsin, added into a 1.5 ml tube at $10^6$/tube, centrifuged for 2 min. at 1,200 rpm at 4° C., and the supernatant was discarded. The pellet was washed two times with 1 ml RNase free PBS(−), the supernatant was removed as sufficiently as possible, and the cells were stored at −80° C. The frozen sample was restored to ambient temperature, genomic DNA was extracted by use of IsoQuick Nucleic Acid Extraction Kit (ORCA Research Inc.). The extracted DNA was dissolved in 10 mM Tris-HCl, 1 mM EDTA, pH8.0 to be stored at 4° C. The DNA content was determined by the fluorescent reader (Cytofluor 2350, Millipore Corporation) with the DNA binding reagent Hoechist 33258, and TRF was prepared by restricted digestion with HinfI treatment. The restricted digestion was carried out as follows. There were added into a 1.5 ml tube, 2 μl of 10×H buffer (TaKaRa, Kyoto), the solution of extracted genomic DNA (2 μg), sterilized water to make up 19 μl, and finally 1 μl of HinfI (6 U/μl, TaKaRa, Kyoto). The reaction was carried out for 3-4 hours at 37° C., and the mixture was stored at −20° C. An gel plate of agarose (type I, Sigma) was prepared so that the agarose concentration at the bridge and the bed would be 1% and 0.8%, respectively. 1×Boyer buffer (50 mM Tris-HCl, 20 mM Sodium Acetate, 2 mM EDTA, 18 mM NaCl, pH 8.0) was used. 0.5 μg/lane of 1 Kb DNA Ladder (GIBCO BRL) as a size marker and the sample in admixture with 3 μl of loading buffer were applied onto the gel, and electrophoresis was carried out for 20 hours at 35 V/cm.

Transblot

Subsequent to the electrophoresis, agarose gel was cut off and stained with ethidium bromide (2 μg/ml) for 15 min., a photograph of the gel was taken on the UV transilluminator. Then the gel was soaked in the denaturation solution (0.2 N NaOH, 0.6 M NaCl) and was shaken at an ambient temperature for 25 min., then it was rinsed with distilled water for once. The gel was soaked again in the neutralizing solution and shaken for 30 min. The gel was placed on a 3 MM filter paper which was set in a blotting equipment filled with 6×SSC, while care being taken not to incorporate any air. Then a nitrocellulose membrane filter (OPTITRAN BA-S85, Schleicher & Schuel) pre-soaked with 6×SSC, a 3MM filter paper pre-soaked with 6×SSC, a paper towel, a glass plate, and a weight (2 kg) was successively placed on the gel, and blotting was performed overnight. Subsequent to the blotting, the membrane filter was soaked in 3×SSC, and the water was drained briefly, then the position of the well was checked on the UV transilluminator. The membrane filter was sandwiched between filter papers, and then it was heated at 80° C. overnight (baking).

Labeling the (TTAGGG)$_4$ Probe and Hybridization

The baked filter was soaked in 3×SSC, then it was soaked in the hybridization buffer (10×Denhart solution, 1M NaCl, 50 mM Tris-HCl (pH 7.4), 10 mM EDTA, 0.1% SDS, 50 μg/ml denatured salmon sperm DNA) and prehybridized by shaking at 65° C. for 3-4 hours. After the prehybridization, the membrane filter was put into a shield bag and then 2 ml of the hybridization buffer to which [$^{32}$P] 5'-terminal labeled (TTAGGG)$_4$ probe (TaKaRa) and 1 μl of 10 mg/ml denatured salmon sperm DNA has been added. The bag was closed in such a way that no bubbles would be incorporated. Then the hybridization was performed by incubating the bag at 50° C. overnight.

Autoradiography

Following the hybridization, the membrane filter was soaked in a washing buffer (4×SSC, 0.1% SDS) and shaken at 55° C. for 15 min. After repeating the above process 4 times, the water on the filter was drained sufficiently, and then the filter was set together with an X ray film (Scientific Imaging Film, Kodak) in the cassette with a intensifying screen, and autoradiography was performed overnight. The smeary appeared TRF density peak was detected with laser densitometer (Ultroscan XL, Pharmacia), and the mobility was determined.

Figure 10:
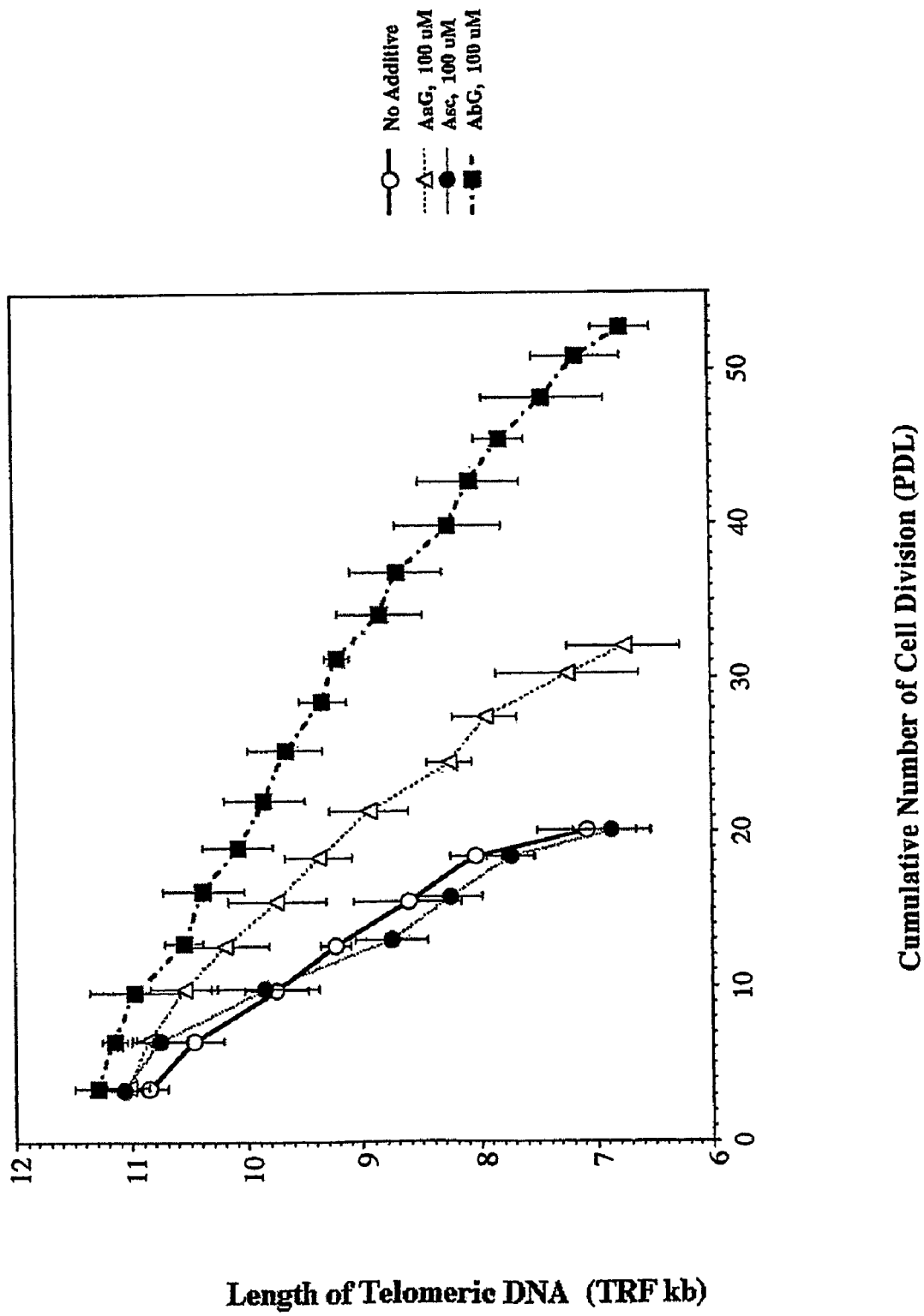
FIG. 10 shows the effect of 2-O-(β-D-glucopyranosyl) ascorbic acid on the reduction speed of telomere lengths. The average reduction speed 225 bp/PDL in the absence of any ascorbic acid derivative was shortened to 94 bp/PDL by the addition of 2-O-(β-D-glucopyranosyl)ascorbic acid. Since the critical telomere length at the time of cell death by aging is known to be constant, it is considered that the ascorbic acid derivative of the invention exhibited a prolonging effect on the life span of the cell line by shortening the speed, by approximately 42%, of the telomere length to reduce to the critical length.

The results are shown in FIG. 10. For comparison, the results of 2-O-(α-D-glucopyranosyl)ascorbic acid, and ascorbic acid were obtained and included in FIG. 10 as well.

The invention claimed is:

1. Isolated and/or purified 2-O-(β-D-Glucopyranosyl) ascorbic acid represented by the following formula (1):

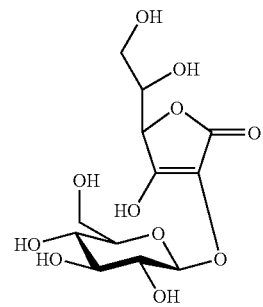

or a biologically acceptable salt or ester thereof.

2. 2-O-(Tetra-O-acyl-β-D-glucopyranosyl)ascorbic acid represented by the following formula (2):

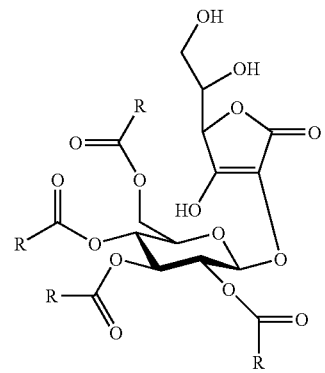

wherein each R in the formula independently represents a $C_{1-5}$ alkyl group.

3. The compound of claim 2, wherein all of the R groups of formula (2) are methyl.

4. A method of producing 2-O-(β-D-glucopyranosyl) ascorbic acid comprising reacting ascorbic acid and a β-D-glucosyl compound in the presence of a β-D-glucosyltransferase that is a cellulase.

5. The method of claim 4, wherein the cellulase is a cellulase from *Trichoderma*.

6. A provitamin C composition comprising 2-O-(β-D-glucopyranosyl)ascorbic acid in the amount of 0.1 to 30 weight percent, and a pharmaceutically, cosmetically, or dietarily acceptable component.

7. A provitamin C composition comprising 2-O-(β-D-glucopyranosyl)ascorbic acid and 6-O-(β-D-glucopyranosyl) ascorbic acid.

8. A pharmaceutical composition comprising the 2-O-(β-D-glucopyranosyl)ascorbic acid or a biologically acceptable salt or ester thereof of claim 1, wherein said 2-O-(β-D-glucopyranosyl)ascorbic acid or biologically acceptable salt or ester thereof is present in the amount of 0.1 to 30 weight percent, and a pharmaceutically acceptable carrier.

9. A cosmetic composition comprising the 2-O-(β-D-glucopyranosyl)ascorbic acid or a biologically acceptable salt or ester thereof of claim 1, and a cosmetically acceptable carrier.

10. The cosmetic composition of claim 9, wherein said 2-O-(β-D-glucopyranosyl)ascorbic acid or biologically acceptable salt or ester thereof is present in the amount of 0.1 to 30 weight percent.

11. A method of producing 2-O-(β-D-glucopyranosyl) ascorbic acid comprising reacting ascorbic acid and a β-D-glucosyl compound in the presence of a β-D-glucosyltransferase, wherein the β-D-glucosyl compound is cellobiose.

* * * * *